United States Patent
Tai et al.

(10) Patent No.: US 8,336,387 B2
(45) Date of Patent: Dec. 25, 2012

(54) MICROFABRICATED IMPLANTABLE WIRELESS PRESSURE SENSOR FOR USE IN BIOMEDICAL APPLICATIONS AND PRESSURE MEASUREMENT AND SENSOR IMPLANTATION METHODS

(75) Inventors: Yu-Chong Tai, Pasadena, CA (US); Po-Jui Chen, Pasadena, CA (US); Damien C. Rodger, Los Angeles, CA (US); Mark S. Humayun, Glendale, CA (US)

(73) Assignee: California Institute of Technology, Pasadena, CA (US)

( * ) Notice: Subject to any disclaimer, the term of this patent is extended or adjusted under 35 U.S.C. 154(b) by 134 days.

(21) Appl. No.: 12/848,837

(22) Filed: Aug. 2, 2010

(65) Prior Publication Data
US 2010/0294041 A1    Nov. 25, 2010

Related U.S. Application Data

(63) Continuation of application No. 11/847,262, filed on Aug. 29, 2007, now Pat. No. 7,900,518.

(60) Provisional application No. 60/841,113, filed on Aug. 29, 2006.

(51) Int. Cl.
*G01L 9/00* (2006.01)
*G01L 9/16* (2006.01)
(52) U.S. Cl. ................ 73/754; 73/715; 73/718
(58) Field of Classification Search ............ None
See application file for complete search history.

(56) References Cited

U.S. PATENT DOCUMENTS

| | | | |
|---|---|---|---|
| 4,287,553 A | 9/1981 | Braunlich | |
| 4,864,463 A | 9/1989 | Shkedi et al. | |
| 5,479,827 A | 1/1996 | Kimura et al. | |
| 5,499,158 A | 3/1996 | Bishop et al. | |
| 5,744,719 A * | 4/1998 | Werner | 73/514.32 |
| 6,312,380 B1 | 11/2001 | Hoek et al. | |
| 6,536,288 B2 * | 3/2003 | Scholz et al. | 73/718 |
| 6,579,235 B1 | 6/2003 | Abita et al. | |
| 6,824,521 B2 | 11/2004 | Rich et al. | |
| 6,855,115 B2 | 2/2005 | Fonseca et al. | |
| 6,890,300 B2 | 5/2005 | Lloyd et al. | |
| 6,926,670 B2 | 8/2005 | Rich et al. | |
| 6,939,299 B1 | 9/2005 | Petersen | |

(Continued)

OTHER PUBLICATIONS

Machay et al., "Endoradiosonde," Nature, vol. 179, pp. 1239-1240 (1957).

(Continued)

*Primary Examiner* — Lisa Caputo
*Assistant Examiner* — Jermaine Jenkins
(74) *Attorney, Agent, or Firm* — Bingham McCutchen LLP

(57) ABSTRACT

A variable capacitor, a microfabricated implantable pressure sensor including a variable capacitor and an inductor, and related pressure measurement and implantation methods. The inductor may have a fixed or variable inductance. A variable capacitor and pressure sensors include a flexible member that is disposed on a substrate and defines a chamber. Capacitor elements extend indirectly from the flexible member. Sufficient fluidic pressure applied to an exterior surface of the flexible member causes the flexible member to move or deform, thus causing the capacitance and/or inductance to change. Resulting changes in resonant frequency or impedance can be detected to determine pressure, e.g., intraocular pressure.

9 Claims, 20 Drawing Sheets

U.S. PATENT DOCUMENTS

| | | | |
|---|---|---|---|
| 6,986,743 | B2 | 1/2006 | Ohama |
| 7,042,698 | B2 | 5/2006 | Won et al. |
| 7,059,195 | B1 | 6/2006 | Liu et al. |
| 7,169,106 | B2 | 1/2007 | Fleischman et al. |
| 7,203,052 | B2 | 4/2007 | Won et al. |
| 7,254,008 | B2 | 8/2007 | Xie et al. |
| 7,290,454 | B2 | 11/2007 | Liu |
| 7,394,641 | B2 | 7/2008 | Won et al. |
| 7,505,946 | B2 | 3/2009 | Chellapilla et al. |
| 7,516,220 | B1 | 4/2009 | Stiert |
| 7,603,706 | B2 | 10/2009 | Donnelly et al. |
| 7,677,107 | B2 | 3/2010 | Nunez et al. |
| 7,725,395 | B2 | 5/2010 | Rui et al. |
| 7,796,371 | B2 | 9/2010 | Xie et al. |
| 7,827,265 | B2 | 11/2010 | Cheever et al. |
| 7,841,940 | B2 | 11/2010 | Bronstein |
| 7,900,518 | B2 | 3/2011 | Tai et al. |
| 7,917,508 | B1 | 3/2011 | Baluja et al. |
| 7,929,805 | B2 | 4/2011 | Wang et al. |
| 8,005,197 | B2 | 8/2011 | Baird et al. |
| 8,019,127 | B2 | 9/2011 | Misra |
| 8,032,481 | B2 | 10/2011 | Pinckney et al. |
| 8,032,483 | B1 | 10/2011 | Haveliwala et al. |
| 8,036,902 | B1 | 10/2011 | Strom et al. |
| 2005/0119636 | A1 | 6/2005 | Haffner et al. |
| 2005/0268722 | A1 | 12/2005 | Tai et al. |
| 2006/0178655 | A1 | 8/2006 | Santini et al. |
| 2006/0247664 | A1 | 11/2006 | Meng et al. |

OTHER PUBLICATIONS

Collins, "Miniature Passive Pressure Transensor for Implanting in the Eye," IEEE Transactions on Biomedical Engineering, BME-14, pp. 74-83 (1967).

Lizon-Martinez et al., "Design of a System for Coninuous Intraocular Pressure Sensor Monitoring," IEEE Transactions on Instrumentation and Measurement, vol. 54, No. 4, pp. 1534-1540 (2005).

Allen, "Micromachined Endovascularly-Implantable Wireless Aneurysm Pressure Sensor From Concept to Clinic," Technical Digest, The 13th International Conference on Solid-State Sensors, Actuators, and Microsystems (Transducers 2005), pp. 275-278 (2005).

Fonseca et al., "Flexible Wireless Passive Pressure Sensors for Biomedical Applications," Technical Digest, The 12th Solid-State Sensors, Actuators, and Microsystems Workshop, pp. 37-42 (2006).

Meng et al., "Implantable Parylene MEMS for Glaucoma Therapy, "Technical Digest, the 3rd IEEE EMBS Special Topic Conference on Microtechnologies in Medicine and Biology (EMBS-MMB2005), pp. 116-119 (2005).

Seo et al., "Design and Simulation of a MEMS-based Comb-Drive Pressure Sensor for Pediatric Post-Operative monitoring Application," Summer Bioengineering Conference, Sonesta Beach, Key Biscayne, Florida, pp. 1239-1240 (2003).

Rosengren et al., "Micromachined Sensor Structures with Linear Capacitive Response," Sensors and Actuators, pp. 200-205, A, 31 (1992).

International Search Report and Written Opinion mailed Aug. 29, 2007 for International Application No. PCT/US07/077156 (12 pages).

Response to Written Opinion dated Sep. 18, 2008 for International Application No. PCT/US07/077156 (14 pages).

International Preliminary Examination Report mailed Oct. 21, 2008 for International Application No. PCT/US07/077156 (10 pages).

* cited by examiner

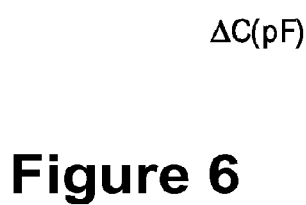
Figure 6
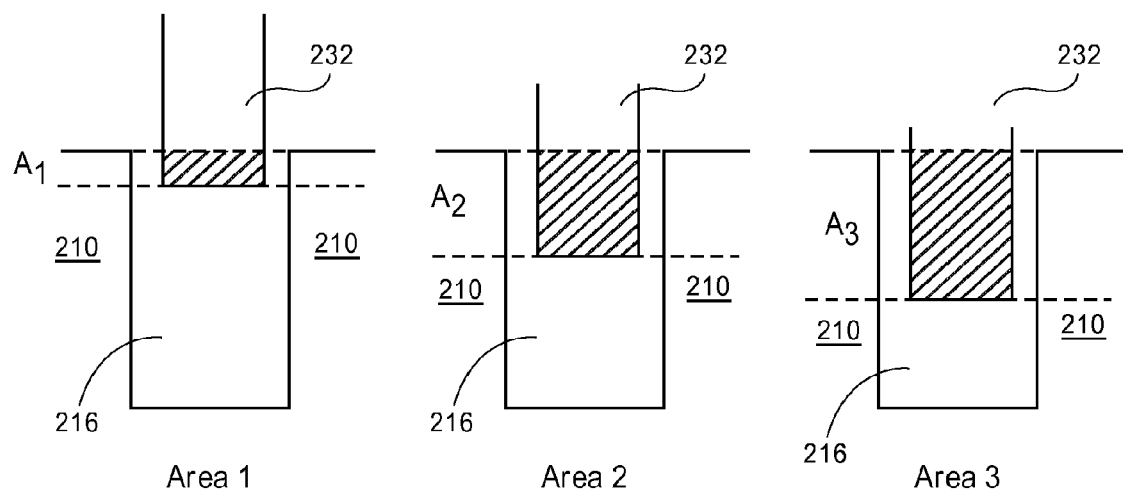
Figure 7     Figure 8     Figure 9

| Pressure sensitivity | 1 mmHg | | |
|---|---|---|---|
| Detection range | 1–50 mmHg | | |
| Design | A (1200) | B (1300) | C (1400) |
| Schematic | 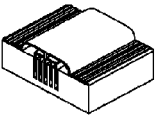 |  |  |
| Variable capacitor scheme | Comb plates (vertical movement) | Comb plates (vertical movement) | Comb plates (vertical movement) |
| Lump inductor scheme | Surface-micromachined (thin lines) | Embedded (HAR thick lines) | Embedded + rollable |
| Overall implant size | $0.5 \times 0.5 \times 3$ mm$^3$ | $0.5 \times 0.5 \times 3$ mm$^3$ | $0.5 \times 0.5 \times 4$ mm$^3$ (after rolled) |
| Capacitance | ~ 25 pF | ~ 31 pF | ~ 127 pF |
| Capacitance change ($\Delta P$ = mmHg) | ~ 0.4 pF | ~ 0.4 pF | ~ 0.4 pF |
| Inductance | ~ 40 nH | ~ 10 nH | ~ 145 nH |
| Resistance | ~ 2.8 Ω | ~ 0.03 Ω | ~ 3.8 Ω |
| Resonance frequency $f_R$ | ~ 159 MHz | ~ 286 MHz | ~ 37 MHz |
| $f_R$ shift $\Delta f$ ($\Delta P$ = mmHg) | ~ 1.6 MHz | ~ 1.8 MHz | ~ 59 KHz |
| $\Delta f/f_R$ | ~ 1 x 10-2 | ~ 6.4 x 10-3 | ~ 1.6 x 10-3 |
| Q factor | ~ 14 | ~ 600 | ~ 9 |

Figure 17

MICROFABRICATED IMPLANTABLE WIRELESS PRESSURE SENSOR FOR USE IN BIOMEDICAL APPLICATIONS AND PRESSURE MEASUREMENT AND SENSOR IMPLANTATION METHODS

CROSS REFERENCE TO RELATED APPLICATION

This application is a continuation of co-pending U.S. application Ser. No. 11/847,262, filed Aug. 29, 2007, which claims priority of U.S. Provisional Application No. 60/841,113, filed on Aug. 29, 2006, the contents of both which are incorporated herein by reference as though set forth in full.

STATEMENT REGARDING FEDERALLY SPONSORED RESEARCH

The U.S. Government has certain rights in this invention pursuant Grant No. EEC-0310723, awarded by the National Science Foundation.

FIELD OF THE INVENTION

The field of the invention relates to pressure sensors and, more particularly, to microfabricated implantable pressure sensors for use in biomedical applications including monitoring of intraocular pressure.

BACKGROUND

Pressure sensor devices have been used to study various physiological conditions in biomedical applications. One known application is to monitor intraocular pressure, for example, in connection with treatment of glaucoma. Glaucoma is a well known ocular disease that affects millions of people. Persons afflicted with this disease require treatment for life. The disease causes visual field loss and if left untreated, may result in permanent loss of vision, and is a primary cause of blindness in the United States and elsewhere.

The exact cause of glaucoma is not known, but it is characterized by pathological changes in the optic disc and nerve fiber of the retina. Studies suggest that development of the disease may be attributable to various factors including elevated intraocular pressure. Normal intraocular pressure typically ranges from about 10 to about 21 mm Hg, e.g., about 15 mm Hg. Intraocular pressures of eyes of patients having glaucoma often exceed 21 mm, although glaucoma may exist when intraocular pressures are at lower levels. Elevated intraocular pressures are believed to be responsible for slowly damaging the optic nerve which, in turn, can cause blind spots in the field of vision. Total blindness may occur if the entire optic nerve is damaged.

One known manner of measuring intraocular pressure is to use an external pressure measurement device that acquires intraocular pressure readings from outside of the eye. One known pressure measurement device is known as a tonometer, which measures an external deformation of an eye and relates that measurement to intraocular pressure. Such external measurement devices, however, may not have the desired level of accuracy since they operate in an external environment rather than within the eye itself. Further, such devices do not provide for continuous monitoring of intraocular pressure since a tonometer must be utilized each time intraocular pressure is to be determined and, therefore, provides discontinuous intraocular pressure monitoring.

It is also known to implant a sensor into an eye for purposes of measuring an electrical parameter related to intraocular pressure, and to use telemetry to obtain an electrical parameter measurement and relate the electrical parameter measurement to intraocular pressure. In one known system, an external instrument generates a signal to remotely energize an in vivo intraocular pressure sensor. The response generated by the in vivo sensor is measured and correlated to intraocular pressure.

For example, referring to FIG. 1, a known intraocular telemetry system 10 includes an external system 20 and an internal or implanted intraocular sensing circuit 30. The external system 20 includes an excitation circuit 21 and a measurement device 22. The sensing circuit 30 typically includes a resistor ($R_{sensor}$) 33 and an inductor ($L_{sensor}$) 34 and a capacitor ($C_{sensor}$) 35. The capacitor 35 may be configured to vary with the intraocular pressure applied to the capacitor 35.

The excitation circuit 21 typically includes an inductor (L) 24. During use, the excitation circuit 20 generates energy, which is delivered to the sensing circuit 30 by inductive coupling between the inductors 24, 34, thereby energizing the sensing circuit 30. The resulting response (e.g., resonant frequency or impedance) of the sensing circuit 30 is measured by the measurement device 22 and correlated to intraocular pressure.

The implanted sensing circuit 30 is essentially an RLC resonance circuit. The resonant frequency and the Quality (Q) factor of the circuit 30 are determined by resistance, capacitance and inductance parameters as provided by Resonant Frequency (f)=$1/(2\pi\sqrt{(LC)})$; and Q Factor=$1/R (\sqrt{(L/C)})$. A change of capacitance causes a shift in resonant frequency of the implanted sensor circuit 30, which can be wirelessly measured by the external measurement device 22. Examples of such intraocular implants and telemetry systems are described in U.S. Pat. No. 6,579,235 to Abita et al., "Passive Silicon Transensor Intended for Biomedical, Remote Pressure Monitoring," by Backlund et al., "A system for wireless intra-ocular pressure measurements using a silicon micromachined sensor," by Rosengren et al., and "A system for passive implantable pressure sensors"; by Rosengren et al.

One known capacitor for use in intraocular pressure sensors is manufactured using MEMS technologies and includes a membrane, a flat bottom portion and a chamber. The capacitor is part of a pressure sensor that is implantable to monitor pressures through a remote telemetry connection. Another known capacitor device used in pressure sensors is referred to as a comb-drive capacitor unit. One known capacitor unit is described in "Design and Simulation of a MEMS-Based Comb-Drive Pressure Sensor for Pediatric Post-Operative Monitoring Applications," by Duck-Bong Seo et al. Seo et al. describe an implantable MEMS-based pressure sensor to monitor pressures through a remote telemetry connection in the context of monitoring pressures of the right side of the heart following surgery. Seo et al. show a flat membrane and a comb drive and explain that a change of overlapping area changes the capacitance of the device, and that no bending or other deformation of the membrane was found for the comb-drive sensor.

While known sensor devices and telemetry systems may provide some improvements over known external pressure measurement devices, they can be improved. For example, certain known sensor devices present performance, biocompatibility, packaging and/or size challenges. Certain known devices also lack sensitivities and detection ranges suitable for various biomedical applications. Further, certain known devices utilize wafer bonding techniques, which typically require additional fabrication time and result in larger or thicker devices. Additionally, bonding often results in reduced yield rate, e.g. due precise component alignment requirements. Thus, devices that are fabricated using wafer bonding are not desirable. Certain known devices also may not be adaptable to commercial fabrication on a large scale. Additionally, the inductor element of the implanted sensor circuit can be improved to provide a more effective sensor circuit and more accurate intraocular pressure determinations. Known devices may also require larger incisions or blades for implantation of sensor devices due to their large size. Such incisions are not desirable. Further, certain known implants require sutures to remain implanted in the eye, which are also not desirable.

Therefore, it would be desirable to have implantable sensor devices that can be fabricated using known micromachining and MEMS technologies. It would also be desirable to have implantable sensor devices that are sufficiently small or miniature in size so that they may be delivered through a needle rather than through a large incision using a blade. It would also be desirable to have sensor devices that may be implanted without the need for sutures and in various locations of an eye. Further, it would also be desirable to have biocompatible and implantable microfabricated sensor devices with improved capacitor and inductor components for enhanced sensitivity, dynamic range and accuracy. It would also be desirable to continuously and passively monitor intraocular pressure by telemetry using such sensor devices. Such capabilities would enhance biomedical applications and pressure-dependent physical conditions and diseases including monitoring of intraocular pressure.

SUMMARY

According to one embodiment, a variable capacitor of a microfabricated implantable pressure sensor includes a substrate, a flexible member having edges disposed on the substrate and a plurality of capacitor elements. The substrate defines a plurality of channels. The flexible member includes a middle portion that is raised above the substrate, thereby defining a chamber between the substrate and the middle portion. The capacitor elements extend indirectly from the flexible member. The capacitor is configured so that changes of fluid pressure causes the flexible member, e.g., the middle portion, to deform, thereby causing capacitor elements to move within respective channels. As a result, capacitance varies due to changes in an overlapping area of the capacitor elements and the substrate.

According to another embodiment, a microfabricated implantable pressure sensor includes a variable capacitor and an inductor. The variable capacitor and the inductor are electrically connected to each other. The variable capacitor includes a substrate, a flexible member and a plurality of capacitor elements. The substrate defines a plurality of channels, and edges of the flexible member are on the substrate. A middle portion of the flexible member is raised above the substrate, thereby defining a chamber. Capacitor elements extend indirectly from the flexible member. Fluid pressure changes on the middle portion cause the middle portion to move, thereby causing the capacitor elements to move within respective channels and causing capacitance to vary with changes in an overlapping area of the capacitor elements and the substrate. An electrical circuit including the variable capacitor and the inductor can generate a detectable resonant frequency shift in response to a change of fluid pressure on an outer surface of the flexible member.

Another embodiment is directed to a microfabricated implantable pressure sensor that includes a substrate, a flexible member disposed on the substrate, a variable capacitor and a variable inductor. A chamber is defined between the substrate and the flexible member, and the variable capacitor and variable inductor are electrically connected to each other. The flexible member carries components of the variable capacitor and also carries components of the variable inductor. With this configuration, the flexible member can be moved in response to fluid pressure changes on an outer surface of the flexible member to vary capacitance and inductance.

A further alternative embodiment is directed to a method of implanting an intraocular pressure sensor at a treatment site in an eye of a patient. The method includes inserting a needle into the eye, delivering an intraocular pressure sensor having a variable capacitor and an inductor through the needle and implanting the intraocular pressure sensor deployed from the needle at the treatment site in the eye.

Another embodiment is directed to a method of measuring intraocular pressure. The method includes generating a signal with an external instrument and energizing a pressure sensor implanted in an eye by the generated signal. The pressure sensor includes an inductor and a variable capacitor that includes a flexible member and capacitor elements extending indirectly from the flexible member and movable within channels defined within a substrate. The method also includes measuring an interaction between the signal generated by the external instrument and the pressure sensor and determining intraocular pressure based on the measured interaction.

In one or more embodiments, capacitor elements extend indirectly from a flexible member by an indirect connection, e.g., by an indirect connector including an intermediate member and a cross bar or member. The capacitor elements are carried by the cross bar or member, which is connected to or extends from an intermediate member, which extends between the flexible member and the cross bar or member. Thus, capacitor elements that move within channels do not extend directly from the flexible member. In one or more embodiments, the middle portion of the flexible member may be deformed in a non-linear manner, e.g., to assume a bowl-like shape, while the intermediate member/cross bar configuration permits the capacitor elements to remain movable within respective channels in a direction that is perpendicular to a plane defined by a top surface of the substrate. The intermediate member and at least one capacitor element may lie within a common vertical plane, and at least one capacitor element may lie within a vertical plane that is offset from and parallel to a vertical plane defined by the intermediate member.

In one or more embodiments, a middle portion of a flexible member may be flexible and resilient (e.g., made of Parylene) so that movement or deformation of the flexible member alters the overlapping area of capacitor elements and the substrate, thereby changing capacitance. Channels in the substrate and capacitor elements may form mating comb structures.

In one or more embodiments, variable capacitor and the inductor components are configured to detect fluid pressure changes with a sensitivity of about 1 mmHg within a fluid pressure range of about 1-50 mmHg.

In one or more embodiments, the inductor may be stationary and have a fixed inductance and be formed by a stack of insulated inductor elements that encircle a variable capacitor. Inductor components may extend through the entire substrate or extend partially through or be deposited on the substrate. The inductor may also be in the form of a ring, which can be collapsed or compressed configuration for delivery through a needle, e.g., a 20-25 gauge needle, and expanded when delivered at the treatment site. Embodiments also provide for suture-less implantation.

BRIEF DESCRIPTION OF THE DRAWINGS

Referring now to the drawings in which like reference numbers represent corresponding parts throughout and in which:

FIG. 6 is a graph showing a relationship between the overlapping area and change in capacitance achieved with the capacitor configuration shown in FIGS. 2-5;

FIG. 7 is a partial cross-sectional view of a substrate and a capacitive element at a first depth within a channel, corresponding to overlapping area A1 in FIG. 6;

FIG. 8 is a partial cross-sectional view of a substrate and a capacitive element at a second depth deeper within a channel, corresponding to overlapping area A2 in FIG. 6;

FIG. 9 is a partial cross-sectional view of a substrate and a capacitive element at a third depth deeper within a channel, corresponding to overlapping area A3 in FIG. 6;

FIG. 17 is a table summarizing expected electrical parameters of microfabricated pressure sensors constructed according to embodiments and having a variable capacitor shown in FIGS. 2-4 and different lump inductor configurations shown in FIGS. 12-15;

DETAILED DESCRIPTION OF ILLUSTRATED EMBODIMENTS

Certain embodiments are directed to a variable capacitor that is a component of a microfabricated implantable pressure sensor for use in various biomedical applications. A variable capacitor constructed according to embodiments includes a substrate having trenches or channels defined therein and a flexible member. A portion of the flexible member is raised above the substrate. Capacitor elements extend indirectly from the flexible member and movable together and simultaneously within the channels, thereby varying capacitance as a result of changing the overlapping area of the substrate and capacitor elements. Certain other embodiments are directed to a microfabricated implantable pressure sensor and configurations of a variable capacitor and an inductor. An inductor may have a fixed or variable inductance. The inductor may be fixed or stationary, or be movable, e.g., with a component of the variable capacitor. Certain other embodiments are directed to a microfabricated sensor having a variable capacitor and a variable inductor that are carried by or embedded within a common flexible member. Certain embodiments are directed to methods of fabricating implantable pressure sensors using surface micromachining and MEMS technologies.

Embodiments advantageously provide implantable pressure sensors that may be fabricated using known micromachining and MEMS technologies and are of a miniature size so that they may be delivered through a needle and implanted in various locations without the need for sutures. Embodiments also advantageously provide biocompatible pressure sensors having variable capacitors, lump/variable inductors with enhanced accuracy, sensitivity and range for use in various biomedical applications including passive monitoring of intraocular pressure using telemetry and other biomedical applications involving, e.g., aneurysms and the brain.

Figure 23:
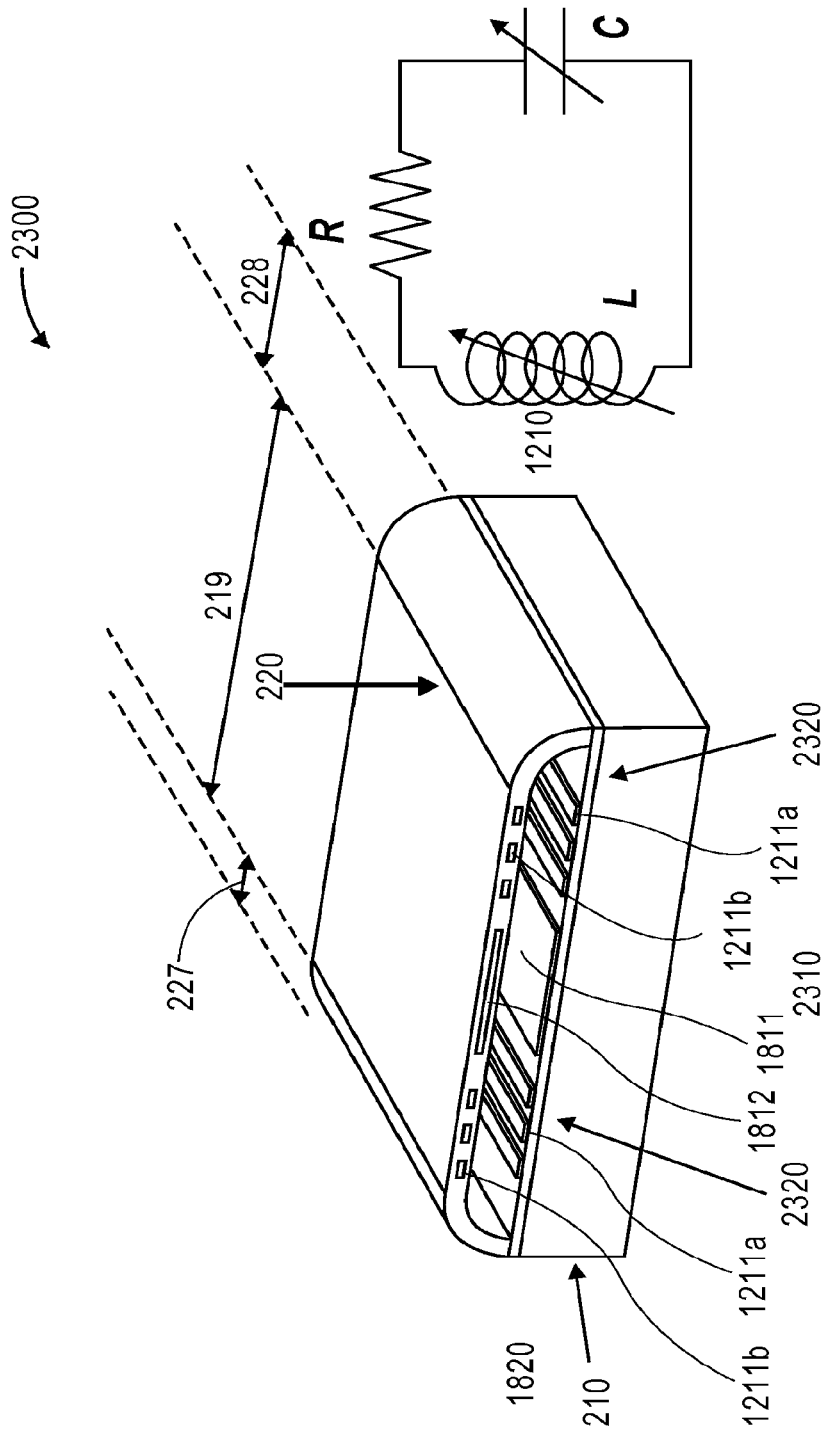
FIG. 23 is a perspective cross-sectional view of a microfabricated implantable pressure sensor having a variable capacitor and a variable inductor according to a further embodiment.
Figure 24:
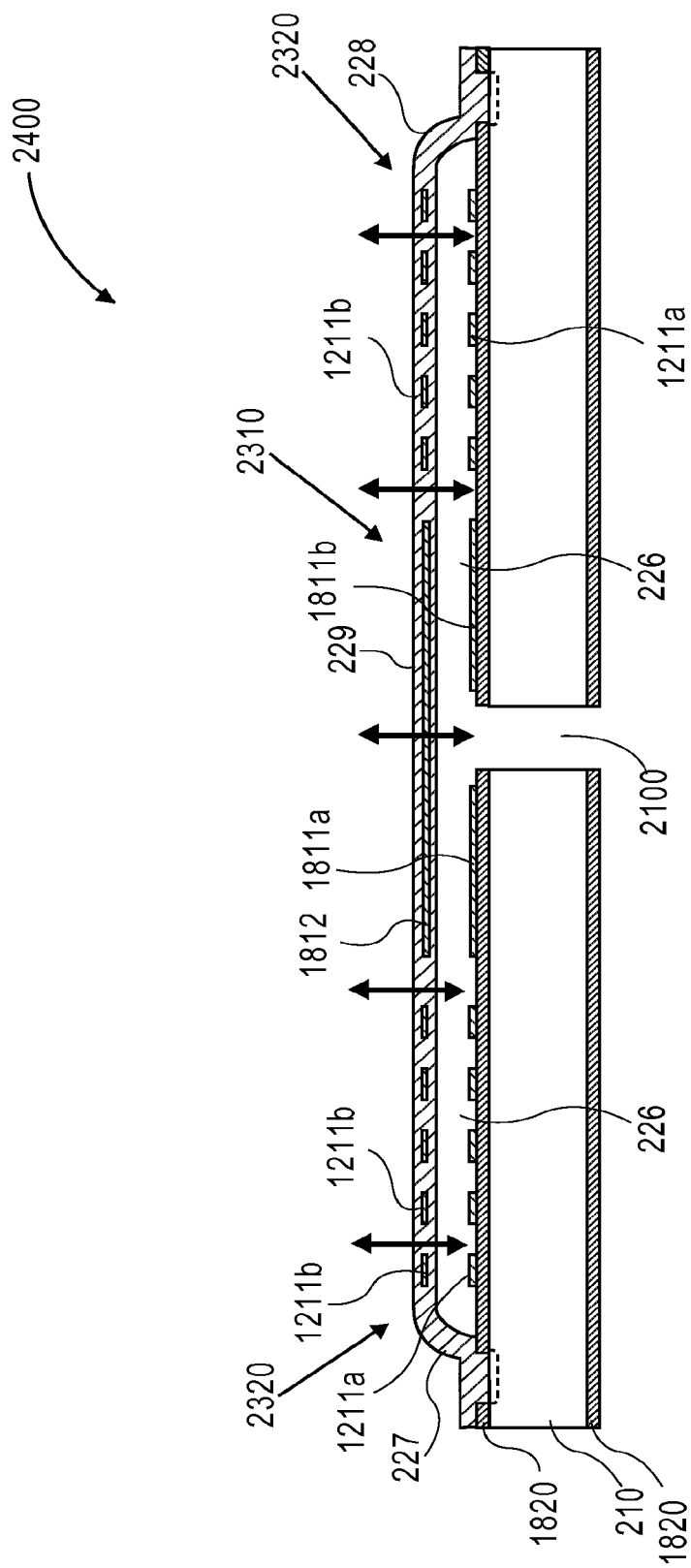
FIG. 24 is a cross-sectional view of a microfabricated implantable pressure sensor having a variable capacitor and a variable inductor according to another embodiment.
Figure 25:
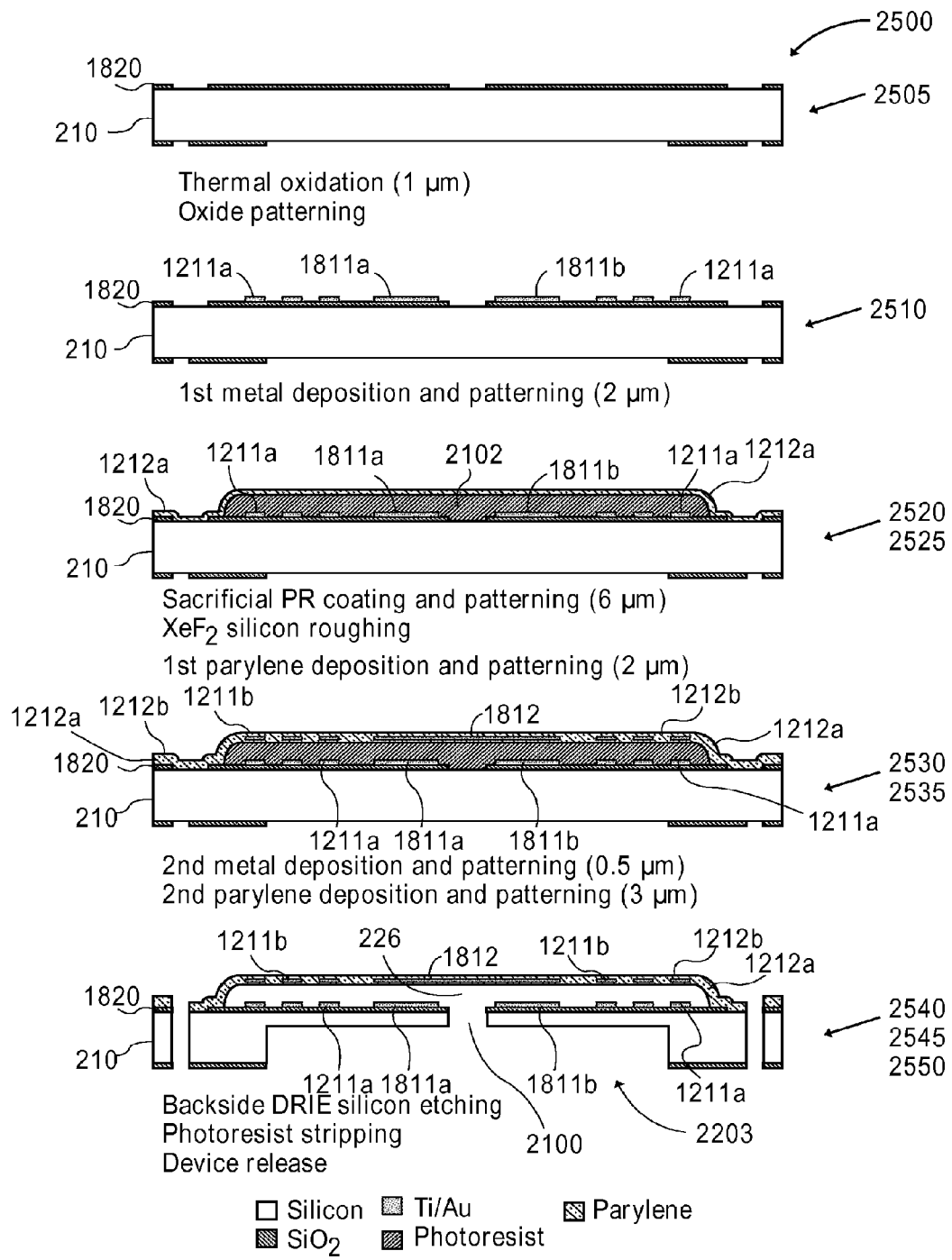
FIG. 25 is a flow diagram illustrating one embodiment of a method of fabricating an implantable pressure sensor having a variable capacitor, a variable inductor and a recessed cavity.

FIGS. 2-10 illustrate embodiments of a variable capacitor of a microfabricated implantable pressure sensor for use in biomedical applications. The variable capacitor includes a flexible member, a portion of which is raised above a substrate and capacitor elements or plates that are moveable within channels or trenches formed within the substrate to vary capacitance. FIGS. 11-17 illustrate different lump or fixed inductor configurations that may be used with a variable capacitor and electrical characteristics thereof and related methods of fabrication. FIGS. 18-21 illustrate embodiments of a microfabricated implantable pressure sensor for use in biomedical applications and having a flexible member, a portion of which is raised above a substrate that does not include channels or trenches, variable capacitance and fixed inductance. FIGS. 23-25 illustrate embodiments of a microfabricated implantable pressure sensor for use in biomedical applications and having a flexible member that carries elements of a variable capacitor and also elements of a variable inductor.

Figure 2:
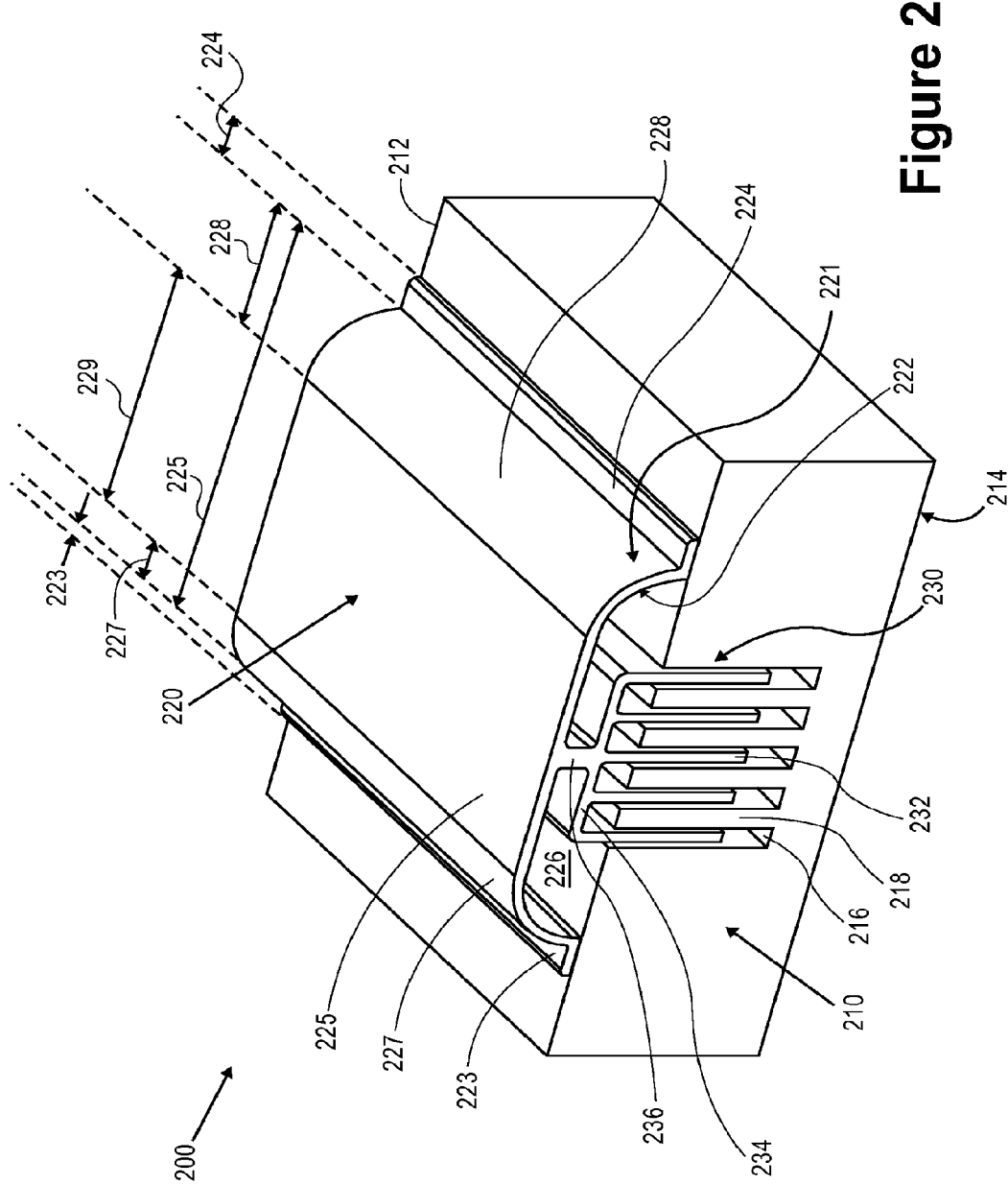
FIG. 2 is a perspective cross-sectional view of a variable capacitor of a microfabricated implantable pressure sensor constructed in accordance with one embodiment.
Figure 3:
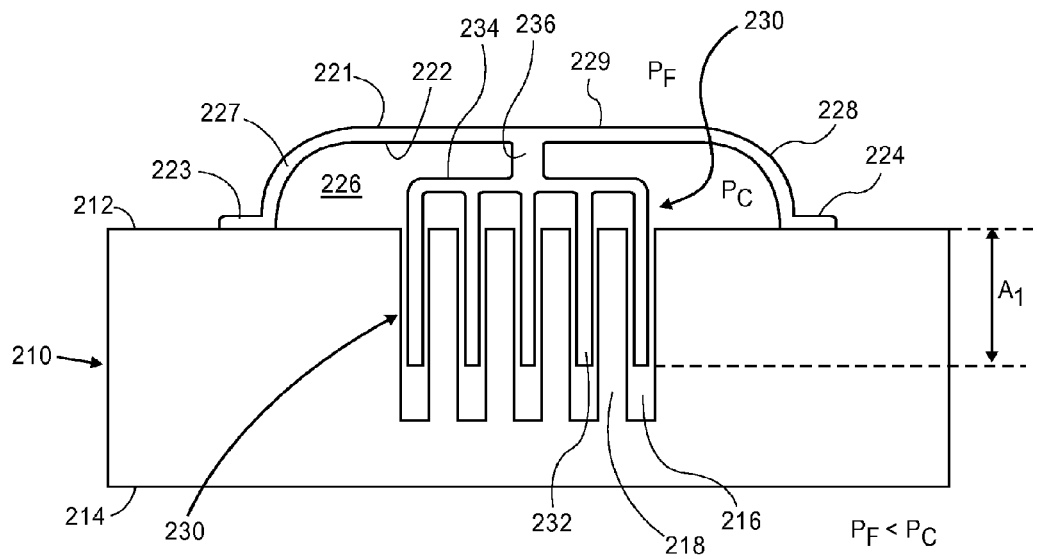
FIG. 3 is a cross-sectional view of the variable capacitor shown in FIG. 2 in which a flexible member is in an initial or relaxed state when external fluid pressure is less than an internal chamber pressure.
Figure 4:
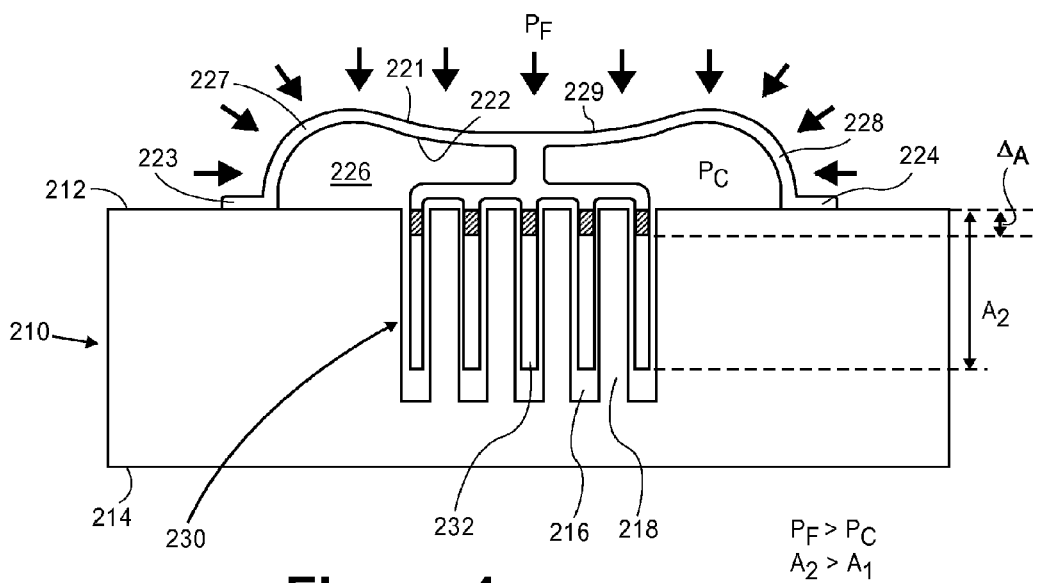
FIG. 4 is a cross-sectional view of a variable capacitor shown in FIG. 2 in which a flexible member is in a compressed or deformed state when external fluid pressure is greater than the internal chamber pressure.

Referring to FIGS. 2-4, a variable capacitor 200 constructed in accordance with one embodiment and configured for use in a microfabricated implantable pressure sensor includes a substrate 210, a flexible member 220 disposed on the substrate 210, and a capacitor component 230 that includes a plurality of capacitor elements 232 extending indirectly from the flexible member 220. The capacitor elements 232 are movable within trenches, grooves or channels (generally channels 216) defined through the substrate 230, e.g., partially through the substrate 230 as shown in FIGS. 2-4. In the illustrated embodiment, all of the capacitor elements 232 are the same length, but other capacitor element 232 configurations may be utilized.

Movement of the capacitor elements 232 to different depths within the channels 216 alters the overlapping area of the capacitor elements 232 and the substrate 220. Changing the overlapping area alters capacitance and the resonant frequency response of a sensor circuit that includes the variable capacitor 200. For example, FIG. 3 illustrates a plurality of capacitor elements or plates 232 positioned at a first depth resulting in an overlapping area A1, whereas the overlapping area increases by ΔA to A2 when the capacitor elements 232 are moved deeper down into the channels 216.

The substrate 210 may be composed of silicon and may be in the form of a wafer having a thickness of about 500 microns. Although this specification refers to silicon, the substrate 210 may be composed of other materials including a conductive polymer or another suitable micromachinable substrate material having sufficiently high conductivity. The substrate 210 has a top surface 212 and a bottom surface 214. One or more channels 216 are formed through the top surface 212 of the substrate, thereby forming corresponding projections, walls or fingers 218. In the illustrated embodiment, the channels 216 and projections 218 form a comb structure.

In the illustrated embodiment, the substrate 210 defines a plurality of channels 216, e.g., five channels 216, and four corresponding projections 218. It should be understood, however, that the substrate 210 may define other numbers of channels 216, e.g., about 3 to 10 channels 216. The number of channels may depend on the capacitor 200 configuration, e.g., the width of the substrate 210 and/or the number of capacitor elements 232. Further, although the illustrated embodiment shows channels 216 and projections 218 that are the same width, the channels 216 and projections 218 may have different widths to provide different variations of capacitance and to accommodate different numbers of channels 216 and different capacitor element 232 configurations.

For example, in embodiments including a 500 micron substrate 210, each channel 216 may have a depth of about 200 microns, a width of about 20 microns, a spacing (projection 218 width) of about 20 microns. The capacitor elements 232 may be movable by about 50 microns within the channels 216, resulting in an overlapping area of the capacitor elements 232 and substrate 210 that may range from about $10^6$ to about $10^7$ square microns. It should be understood that other dimensions and configurations may be utilized as necessary.

The flexible member 220 includes an outer or top; surface 221 and an inner surface 222. First and second edges or bottom surfaces 223, 224 are disposed on, connected to, formed on, or sealed to the top surface 212 of the substrate 210. During fabrication of the variable capacitor 200, another material or coating, such as a layer of silicon dioxide (not shown in FIGS. 2-4), may be applied on the top surface 212 of the substrate 210. Thus, the edges 223, 224 of the flexible member 220 may be in direct contact with a silicon dioxide layer rather than the top surface 212. For ease of explanation and illustration, FIGS. 2-4 show edges 223, 224 being disposed on, connected to or formed on the top surface 212 of the substrate 210, whether such contact is direct or indirect as a result of an intermediate silicon dioxide layer.

The flexible member 220 also includes a middle portion 225 that extends between the first and second edges 223, 224. The middle portion 225 is raised above the top surface 212 of the substrate 210, thereby defining an inner space or chamber 226 between the top surface 212 and the inner surface 222 of the flexible member. The capacitor 200 is eventually sealed so that the inner space or chamber 226 is also sealed and has a fixed internal or chamber pressure ($P_c$).

In the illustrated embodiment, the middle portion 225 includes first and second arcuate or "shoulder" sections 227, 228. In the illustrated embodiment, each shoulder section 227, 228 extends inwardly and upwardly from respective first and second edges 223, 224 to a middle section 229 that extends between the shoulder sections 227, 228. In the illustrated embodiment, the middle section 229 is flat and parallel to the top surface 212 of the substrate 210, whereas the shoulder sections 227, 228 extend upwardly in some manner (e.g., as a result of having an arcuate shape) so that the middle section 229 is raised above the substrate 210. It should be understood that the middle portion 225 may have other shapes and that the shoulder sections 227, 228 may be arcuate or shoulder shapes or other shapes as necessary in order to raise the middle section 229 above the substrate 210.

The flexible member 220 is made of a material that allows the middle portion 225, e.g., the middle section 229 and/or one or more shoulder sections 227, 228 depending on the capacitor 200 configuration and fluid pressure application, resulting in deformation, deflection or bending of the middle portion 225 under fluid pressure ($P_f$) if the fluid pressure is greater than the internal chamber pressure (Pc) (as shown in FIG. 4). The flexible member 220 may be resilient to return from a deformed shape (as shown in FIG. 4) to an initial or relaxed shape (as shown in FIG. 3) when the external fluid pressure is less than the internal chamber pressure.

For this purpose, the flexible member 220 may be composed of a material having a suitable Young's modulus of about 1 GPa to about 10 GPa, e.g., about 4 GPa. One example of a suitable material for the flexible member 120 is Parylene, e.g., Parylene C, D, N, F, HT, A and AM. For ease of explanation, reference it made to the flexible member 220 being made of a polymer or Parylene, but it should be understood that the flexible member 120 may be composed of other suitable materials that provide desired flexibility and/or resiliency attributes. Selection of flexible member 120 materials may also depend on, for example, ease of micromachining, CMOS/MEMS process compatibility and biocompatibility (e.g., USP Class VI implantable grade).

In one embodiment, the flexible member 220 may be made of Parylene, have a width of about 500 microns, and the shoulder sections 227, 228 may be configured so that the middle section 229 is raised above the top surface 212 of the substrate 210 by about 10 microns. The middle portion 225 may be moved or deflected by about 10 microns towards the substrate 210. It should be understood that these dimensions are provided as one example of how a variable capacitor 200 having a raised flexible member 220 may be implemented, and other configurations may be utilized for different applications.

Figure 5:
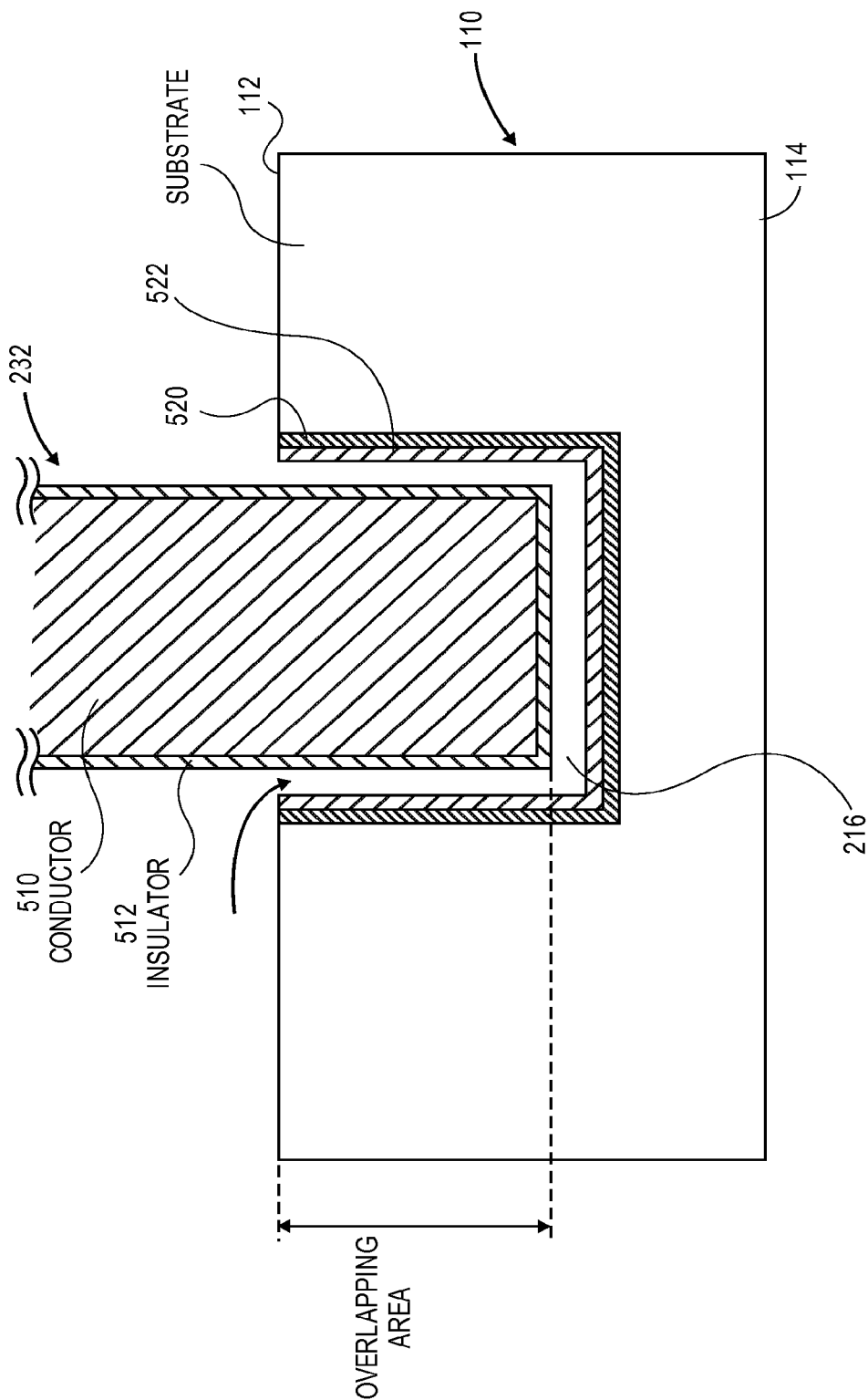
FIG. 5 further illustrates a channel formed within a substrate and a capacitor element extending from a flexible member and being moveable within the channel to alter the overlapping area and capacitance.

Referring to FIGS. 2-4, and with further reference to FIG. 5, capacitor elements 232 may be in the form of fingers or plates that extend indirectly from the flexible member 220 and are arranged in a comb structure. In the illustrated embodiment, capacitor elements 232 extend directly from, or are carried by, one or more cross bars or members 234. An intermediate member 236 extends between the flexible member 220 and the cross bars or members 234. FIGS. 2-4 illustrate an embodiment that includes a single intermediate member 236 that connects the middle section 229 of the flexible member 220 and the cross-bar member 234. Portions of the chamber 226 are defined by the inner surface 222 of the middle section 229, cross bar members 234, the intermediate member 236 extending between the flexible member and a cross bar member 234.

According to one embodiment, the number of intermediate members 236 is less than the number of capacitor elements 232. In the illustrated embodiment, a single intermediate member 236 joins the middle section 229 and a cross bar 234 that carries a plurality of capacitor elements 232. This configuration advantageously provides a flexible member 220 having sufficient flexibility and advantageously provides linear or vertical movement or substantially linear or vertical movement of capacitor elements 232 within channels 216 even when the flexible member 220 is deformed.

More specifically deformation of the flexible member 220 by fluid pressure results in downward movement of the flexible member and downward movement of the intermediate member 236 extending from the flexible member. This results in downward movement of the capacitor elements 232 carried by the cross bar 234, which extends from the intermediate member 236. The structural configuration of embodiments advantageously prevents outward bowing of capacitor elements 232 that may result if the capacitor elements 232 extended directly from the flexible member 220 (i.e., without any intermediate member 236, as in known comb structure devices), thereby causing capacitor elements 232 to scrape against inner surfaces of the channels 216, or causing the capacitor elements 232 to not be positioned within the channels 216 depending on the configuration of the capacitor. Thus, embodiments advantageously utilize an intermediate member 236/cross bar 234 configuration so that capacitor elements 232 extend indirectly from the flexible member, thereby preventing the capacitor elements 232 from being pushed out at an angle when the flexible member 220 is deformed, e.g., in a bowl-like shape, by fluid pressure.

It should be understood that other structural configurations may be utilized while achieving these advantages. For example, rather than having a single intermediate member 236, other numbers of intermediate members 236 may be utilized so long as the number of intermediate members 236 provides sufficient flexibility and maintains the vertical orientation of the capacitor elements 232 when the flexible member 220 is deformed.

In the illustrated embodiment, at least one capacitor element 232 is in-line with, or within the same vertical plane defined by, the intermediate member 236, and at least one other capacitor element 232 is within a vertical plane that is offset from the vertical plane defined by the intermediate member 236. In the illustrated example, the middle capacitor element 232 lies within the same vertical plane defined by the intermediate member 236, and the other capacitor elements lie within different vertical planes and are parallel to the plane defined by the intermediate member 236 and the middle capacitor element 232. In other embodiments, the capacitor elements 232 may be arranged so that no capacitor element 232 is in-line with or within the same vertical plane defined by the intermediate member 236, but all capacitor elements 232 are parallel to the plane defined by the intermediate member 236. The particular configuration utilized may depend on, e.g., the number of intermediate members 236, the number of capacitor elements 232 and the arrangement of these components.

Referring to FIG. 5, capacitor elements 232 are configured and have a suitable shape and size so that they may move with the flexible member 220 within channels 216, e.g., within channels 216 of a corresponding substrate 120 comb structure. According to one embodiment, a capacitor element 232 is a conductive material 510, such as a metal, and may be optionally coated with an insulation material 512. In another embodiment, the capacitor element 232 may include a metal coating that is applied over a conductive, non-metallic material. A channel 216 may also include an insulative coating 520 and a conductive or metal coating 522 that is applied within the channel 216 using metallization.

During use, the flexible member 220 having capacitor elements 232 extending there from is used as a variable capacitor electrode, and the substrate 110 is used as a ground electrode. If the internal chamber 226 pressure is greater than the external fluid pressure, then the flexible member 220 will not be deformed or bent and will retain its original or initial shape. If the fluid pressure exceeds the chamber 226 pressure, then the middle portion 229, e.g., the middle section 225 of the flexible member 220, will be deformed or deflected by the fluid pressure. The flexible member 220 may be sufficiently thin (e.g., about 10 microns) so that the amount of deflection of the middle portion 229 is proportional to the difference between the external fluid pressure and the internal chamber pressure, $((\delta)(\alpha)(\Delta P))$. At the same time, the position of the capacitor elements 232 extending from the flexible member 220 is changed, i.e., the capacitor elements 232 move with the moving flexible member 220.

As a result, the effective overlapping area between interdigitated electrodes is changed which, in turn, alters the capacitance across the electrodes. More specifically, the capacitance increases as the capacitor elements 232 are moved deeper within respective channels 216 and the overlapping area of the substrate 220 and the capacitor elements 232 increases, and capacitance decreases as the capacitor elements 232 are moved to a shallower depth within the channel 216 and the overlapping area of the substrate 220 and the capacitor elements 232 decreases.

For example, referring to FIG. 6, capacitor elements 232 may assume an initial, relaxed position, generally illustrated as (0,0). The initial position may be the capacitor elements 232 being positioned partially within respective channels 216. Alternatively, a capacitor element 232 may be positioned outside above the channels 216, e.g., above the top surface 112 in the illustrated example. The initial relaxed position may depend on the variable capacitor 200 configuration, e.g., how far the flexible member 220 may be deflected or deformed and the length of the capacitor elements 232.

FIG. 7 illustrates one example in which the initial, relaxed position is a position in which distal portions of capacitor elements 232 are positioned partially inside respective channels 216. When the chamber 226 pressure is greater than the external fluid pressure, the flexible member 220 is in its initial, relaxed state, and the capacitor elements 232 are positioned at a first depth within the channels 216. This arrangement results in an initial overlapping area (A1) of the distal portions of the capacitor elements 232 and the substrate 210, and a corresponding capacitance C1.

Referring to FIGS. 6 and 8, as fluid pressure on the outer surface 221 of the flexible member 220 increases, the fluid pressure will exceed the internal chamber 226 pressure, causing the flexible member 220 to bend or deflect towards the substrate 210. This causes the capacitor elements 232 to be moved from the initial depth to a second, deeper depth within the channels 216. This movement of the flexible member 220 results in the overlapping area of the capacitor elements 232 and the substrate 210 to increase from A1 to A2 and results in a corresponding increase in capacitance from C1 to C2.

Similarly, as shown in FIGS. 6 and 9, as fluid pressure increases further, the flexible member 220 will bend or deflect towards the substrate 210 to a greater degree, thereby moving the capacitor elements 232 to a third, depth within the channels 216. This movement results in the overlapping area of the capacitor elements 232 and the substrate 210 to increase from A2 to A3 and a corresponding increase in capacitance from C2 to C3.

The capacitance behavior of this structure can be expressed as $\Delta C=(\epsilon A/d)\ (\alpha)(\delta)(\alpha)(\Delta P)$, where $\Delta C$=change of capacitance for a deflection of the flexible member 220 and corresponding movement of capacitive elements 232 within channels 216; $\epsilon$=permittivity of the channel 216 space; A=overlapping area of capacitor elements 232 and substrate 210; d=distance between a conductive portions 510 of a capacitor element 232 and a conductive layer 520 of the channel 216 of the substrate 210; $\alpha$ is the proportional symbol and $\Delta P$=the change in fluid pressure on the flexible member 220.

Figure 10:
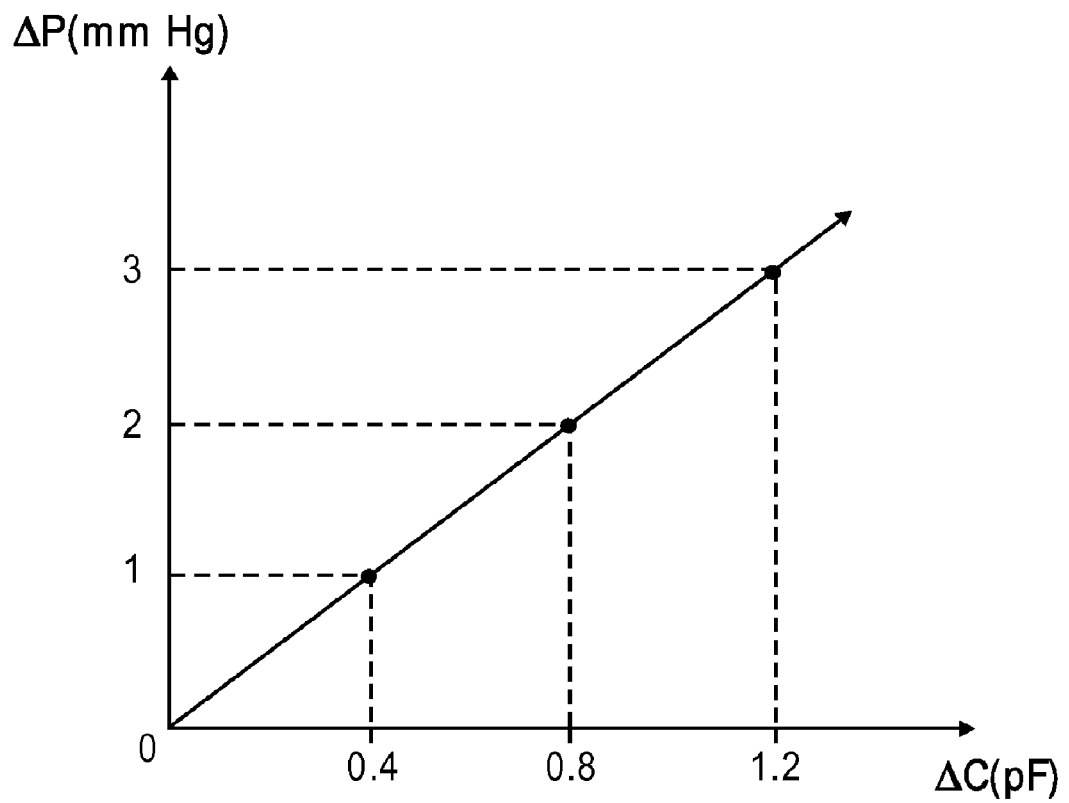
FIG. 10 is a graph showing a relationship between changes of capacitance and pressure, and measurement sensitivity achieved with the capacitor configuration shown in FIGS. 2-5.

FIG. 10 illustrates how a change in capacitance may be correlated to a change in fluid pressure on the flexible member 220. In the illustrated example, a 0.4 pF change of capacitance corresponds to a pressure change of 1 mm Hg. Thus, embodiments are capable of pressure measurements with 1 mm Hg sensitivity.

Figure 1:
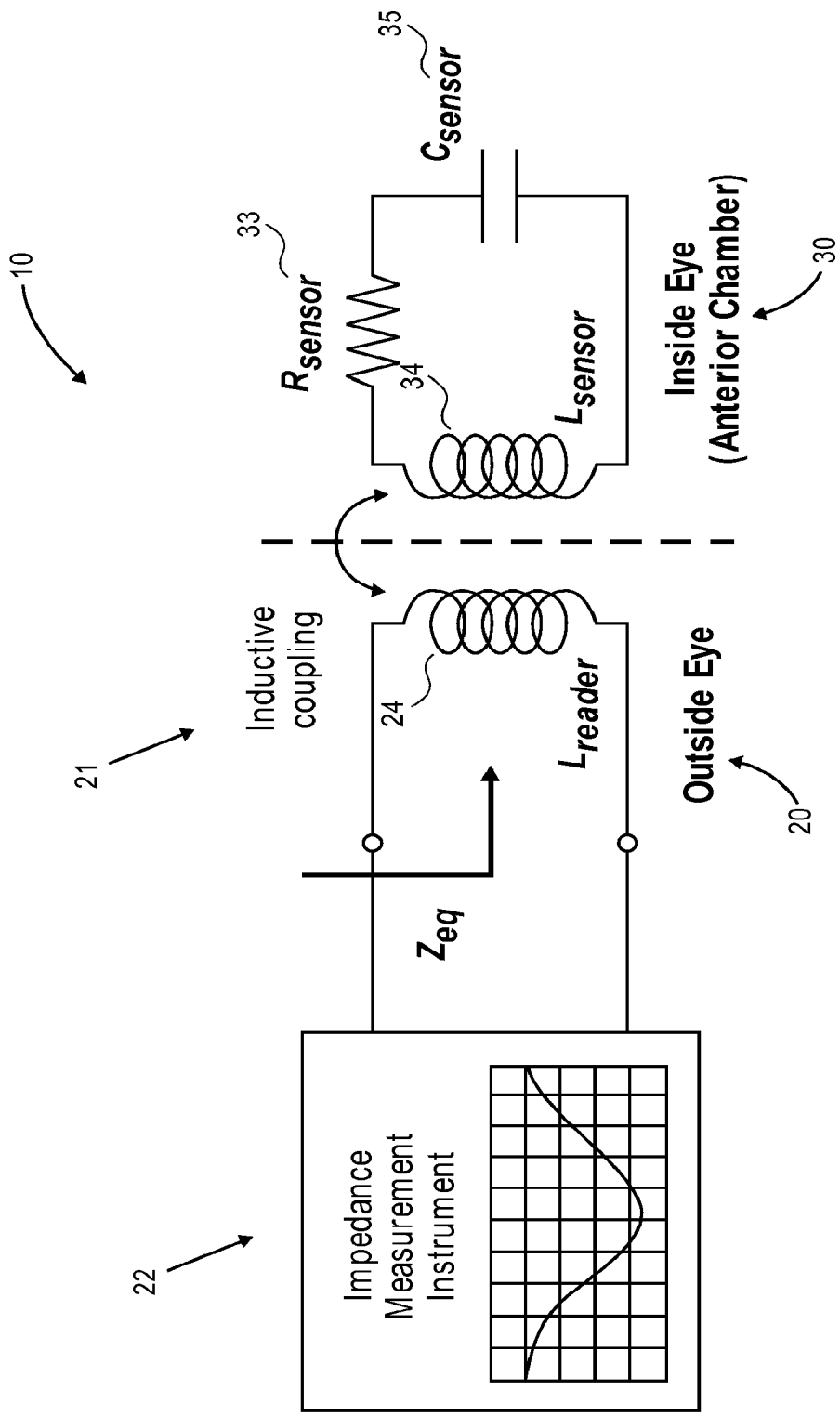
FIG. 1 illustrates a known telemetry system for monitoring intraocular pressure.

The total capacitance may be expressed as C(total)=C0+$\Delta C(\Delta P)$ where C(total)=total capacitance; C0=a fixed capacitance (when $\Delta P$=0); $\Delta C$=change of capacitance as a function of pressure difference $\Delta P$ on the flexible member 220 and $\Delta P$=pressure difference on the flexible member 220. The total capacitance should be sufficiently high to allow a variable capacitor 200 to be used in telemetry systems (e.g., in the system generally illustrated in FIG. 1). Total capacitance may be increased by increasing the area of the capacitor elements 232 (larger electrode overlapping area), providing a larger number of capacitor elements 232, structuring the flexible member 220 so that it may be deflected to greater depths within channels 216 to increase overlapping areas, and decreasing the distance between interdigitated electrodes.

Additional considerations for effective telemetry include having a pressure sensor with sufficiently high inductance and sufficiently high coupled capacitance in order to allow the resulting resonant frequency of the sensor circuit to lie within a reasonable detection range. For example, the resonant frequency of an implantable sensor circuit should lie between 10-500 MHz for telemetry involving biomedical applications. For this purpose, in addition to having a variable capacitor 200 and sufficient capacitance as discussed above with reference to FIGS. 1-10, microfabricated implantable pressure sensors should also have inductor elements that allow the sensor to be implantable and provide electrical characteristics (e.g. resonant frequency) suitable for use in biomedical applications and telemetry. FIGS. 11-15 illustrate different embodiments of pressure sensors having lump inductors or inductors having a fixed inductance.

Figure 11:
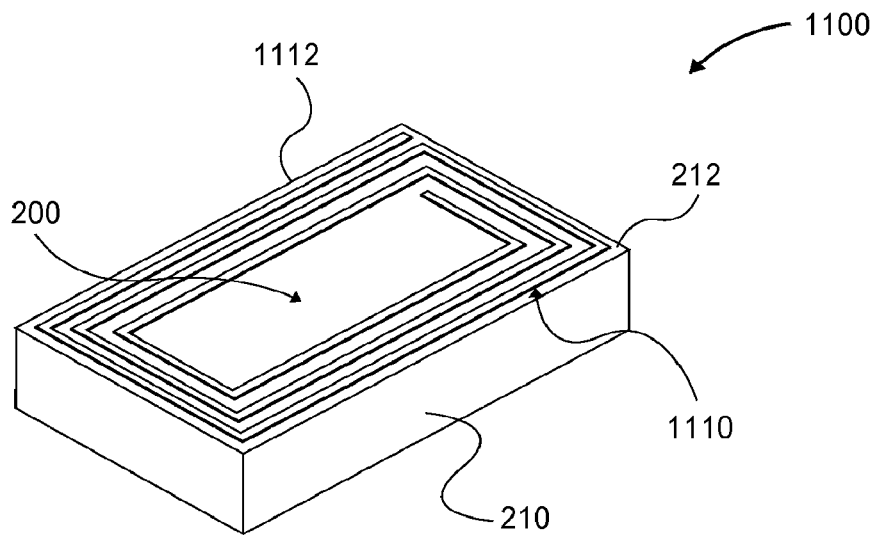
FIG. 11 is a perspective view of a lump inductor of an implantable pressure sensor having integrated metal lines according to one embodiment.

FIG. 11 illustrates a lump inductor 1110 constructed in accordance with one embodiment for use in a microfabricated implantable pressure sensor 1100 includes a variable capacitor 200 (not illustrated in FIG. 11 for clarity). Further, FIG. 12 is a perspective cross-sectional view illustrating metallic layers 1211 along two sides of the variable capacitor 200 in order to illustrate how the variable capacitor 200 and the inductor 1210 may be integrated within the sensor 1200, but it should be understood that the stacked metallic layers 1211 are arranged around the variable capacitor 200.

The inductor 1110 is formed by metal lines 1112 that are integrated within the top surface 212 of the substrate 210 and surround the variable capacitor 200. In the illustrated embodiment, a single wire 1112 is wound in a spiral pattern around the variable capacitor 200. One example implementation of the inductor 1110 shown in FIG. 11 may include a metallic line or element 1112 having a thickness of about 2 microns, a width of about 20 microns, and being wound to form about five overlapping sections. Overlapping metal lines 1112 may be spaced apart by about 10 microns.

Figure 12:
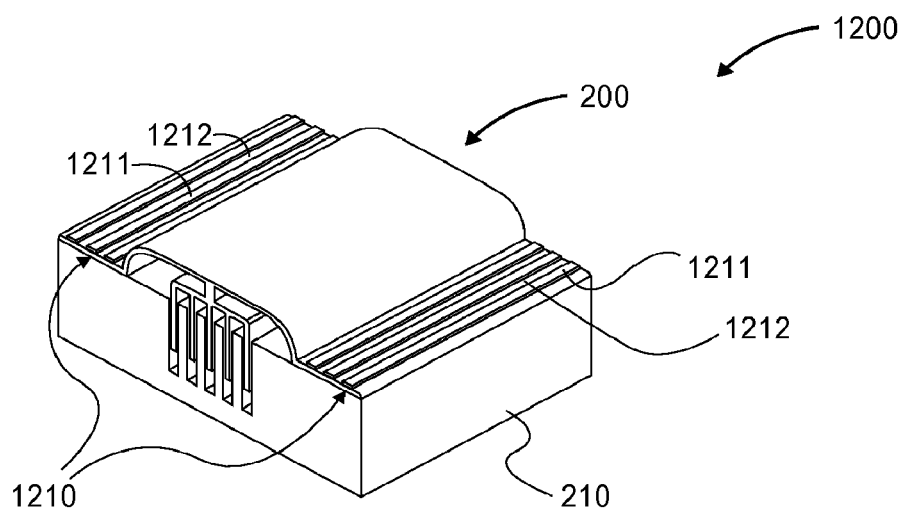
FIG. 12 is a perspective cross-sectional view of a lump inductor constructed having stacked metallic layers separated by insulative material according to another embodiment.

Referring to FIG. 12, in another embodiment, a microfabricated pressure sensor 1200 includes an inductor 1210 that is formed as a stack of metallic layers 1211 that are fabricated using surface-micromachining methods. In this embodiment, the inductor 1210 is arranged so that alternating insulative layers 1212 and metallic layers 1211 are stacked together. This inductor configuration may be particularly suited for configurations that required increased lump inductance and lump capacitance. The insulative layer 1212 may be a polymer such as Parylene or the same material that is used to form the flexible member 220. All of the metallic layers 1211 may be embedded within an insulative material 1212, or a top metallic layer 1211 may be exposed (as shown in FIG. 12). In one embodiment, the inductor 1210 may include a stack of about two to four metallic layers 1211. The thickness of a metallic layer 1211 may be about 2 microns, a width of a metallic layer 1211 may be about 20 microns and the thickness of the insulative layer 1212 between metallic layers 1211 may be about 2 microns.

Figure 13:
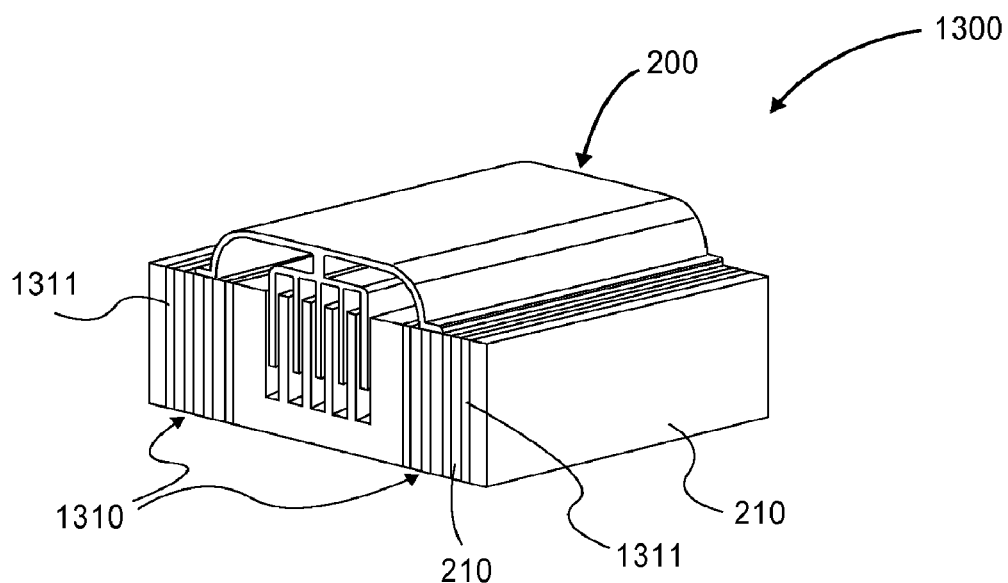
FIG. 13 is a perspective cross-sectional view of a lump inductor constructed having metallic elements formed through or embedded within a substrate according to another embodiment.

Referring to FIG. 13, it may be desirable to increase inductance while reducing resistance in order to increase the quality (Q) factor for higher sensing capabilities in terms of both sensitivity and sensing distance. For this purpose, a microfabricated pressure sensor 1300 may include a variable capacitor 200 (as shown in FIGS. 1-10) and a high aspect ratio inductor 1310. FIG. 13 is a perspective cross-sectional view illustrating the inductor 1210 elements along two sides of the variable capacitor 200 in order to illustrate how the variable capacitor 200 and the inductor 1310 may be integrated within the sensor 1300, but it should be understood that the metal lines 1311 are arranged around the variable capacitor 200.

The inductor may include thick metal lines 1311 that fill channels 216 that are formed completely through the portions of the substrate 210. In other embodiments, the metal lines 1311 may fill channels 216 formed partially through the substrate 210 depending on the desired inductance and resistance. The high aspect ratio inductor 1310 configuration shown in FIG. 13 is well suited to maximize the capacitance and inductance of the sensor 1300 while reducing resistance as a result of the dimensions of the thick metal lines 1311 based on the expression R=ρL/A, where ρ=resistivity of the metal material, L=length of the metal line, and A=area of the metal line. For example, the thickness of the substrate 210 may be about 500 microns, metal lines 1311 may extend through the substrate 210 to have a depth that is also about 500 microns, the width of the metal lines 1311 may be about 20 microns and the metal lines 1311 may extend along the length of the substrate 210, e.g., about 3 millimeters.

Figure 14:
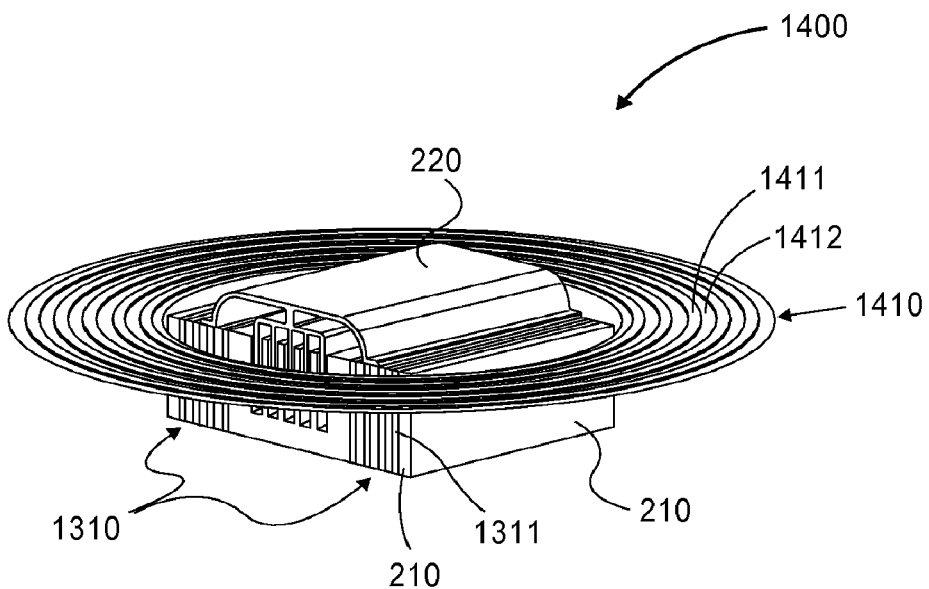
FIG. 14 is a perspective view of a lump inductor having metallic elements formed through or embedded within a substrate and a foldable or rollable inductor sheet or ring according to a further embodiment.
Figure 15:
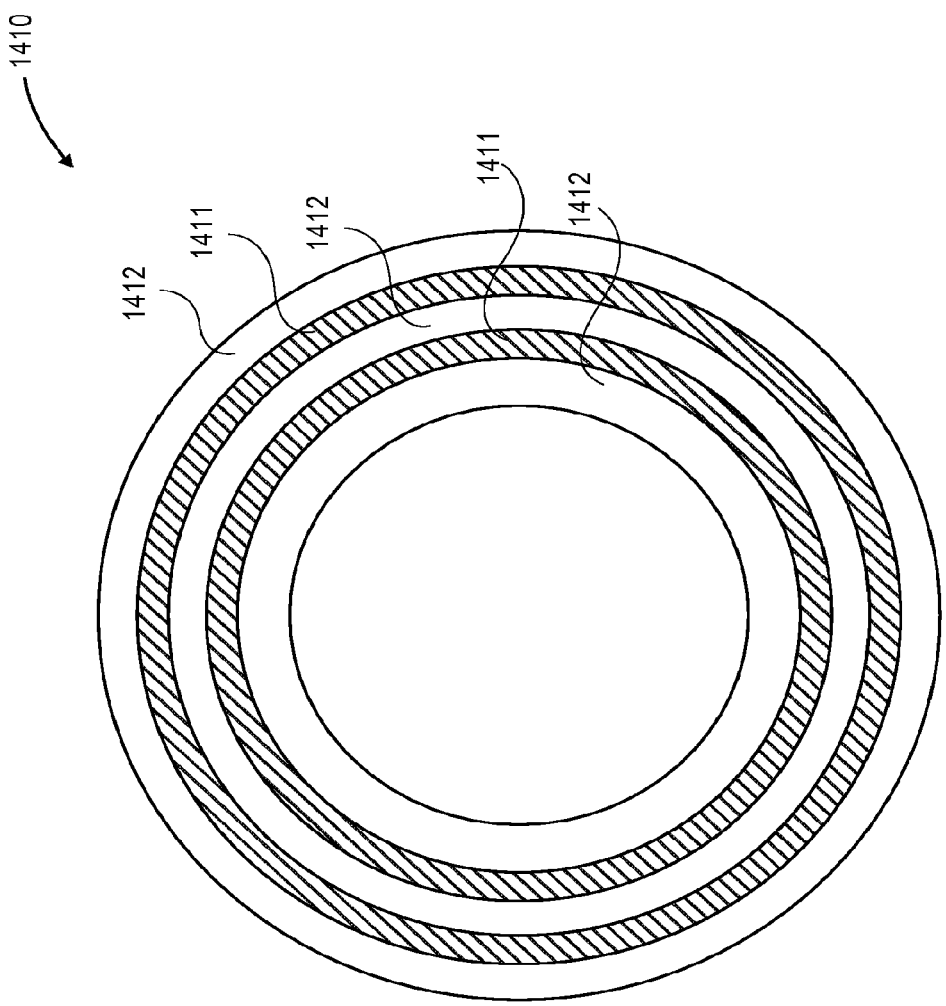
FIG. 15 further illustrates a structure of the foldable or rollable inductor sheet or ring of the inductor shown in FIG. 14 in accordance with one embodiment.

Referring to FIGS. 14 and 15, in another embodiment, a microfabricated pressure sensor 1400 may include a variable capacitor 200 and a lump inductor 1410 in the form of an inductor sheet. For purposes of illustration, not limitation, the sensor 1400 is shown as having an inductor sheet 1410 that is coupled to metal lines 1311 of the high aspect ratio inductor 1310 shown in FIG. 13. In other embodiments, the inductor sheet 1410 may be used as the sole inductor element, or in combination with other types of inductors, e.g., as shown in FIGS. 11 and 12. Thus, FIGS. 14 and 15 are provided as one example of how embodiments may be implemented.

In the illustrated embodiment, the inductor sheet 1410 has a circular shape (when in an expanded or relaxed shape) and includes alternating metallic layers 1411 and insulative layers 1412. The metallic layers 1411 may be platinum, titanium and gold, or another suitable biocompatible metal or conductive materials. The insulative layers 1412 may be a polymer such as Parylene.

The inductor sheet 1410 is preferably configured for implantation through a clinical gauge needle (e.g., having a 20-25 gauge size). For this purpose, the inductor sheet 1410 may be configured to assume a stressed or compressed shape when being delivered through a needle and an expanded or relaxed shape after the sensor 1400 is deployed from the needle and implanted. For example, the inductor sheet 1410 may be rolled or folded while positioned within the needle and may expand to assume a circular shape (as shown in FIGS. 14 and 15) when the pressure sensor 1400 is deployed from the needle.

Figure 16A:
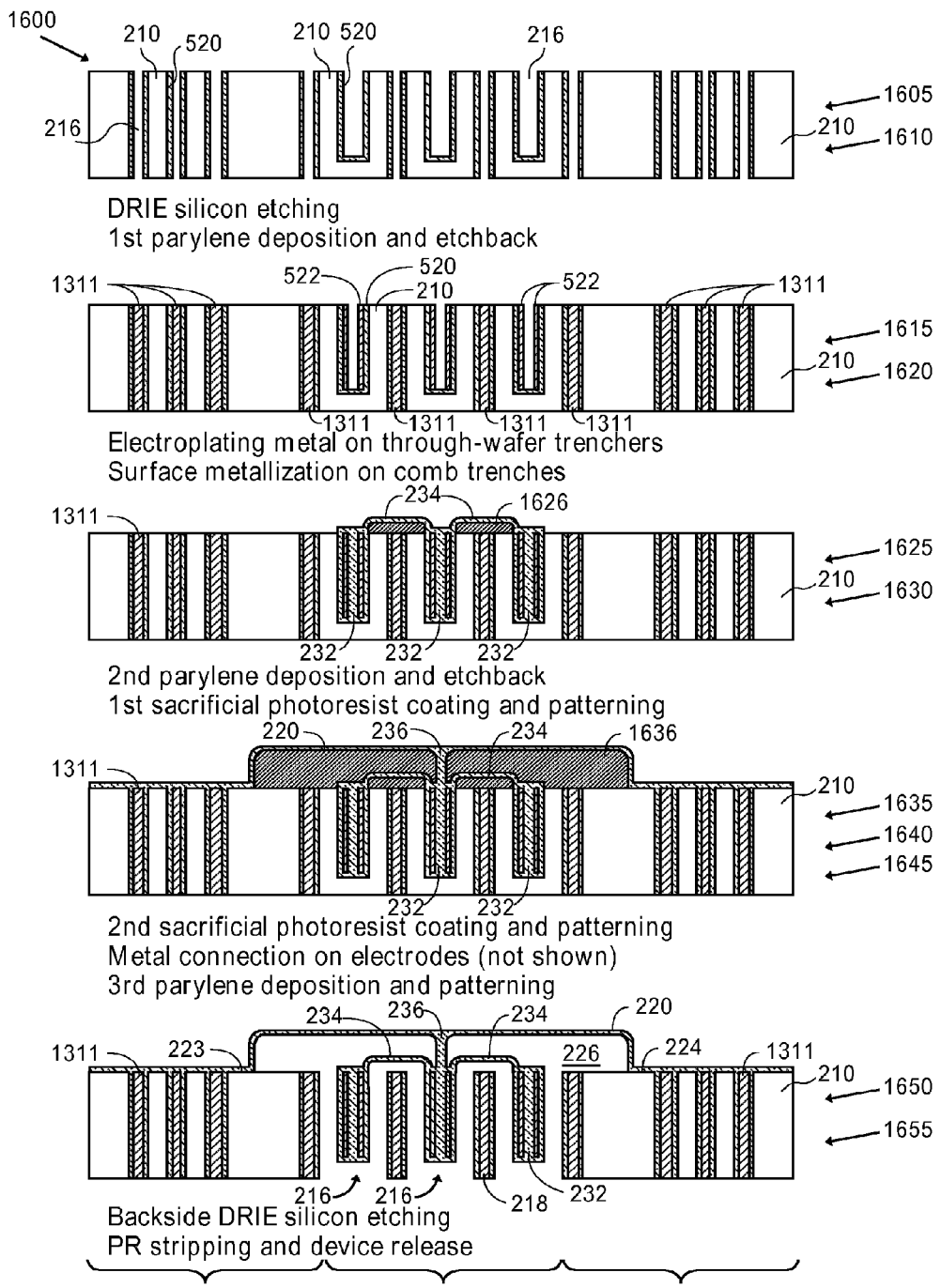
FIG. 16A is a flow diagram illustrating one embodiment of a method of fabricating an implantable pressure sensor having a variable capacitor and a lump inductor in which inductor elements are formed by metal lines extending through a substrate.

FIG. 16A illustrates an embodiment of a method 1600 of fabricating a micromachined pressure sensor having a variable capacitor (e.g., as shown in FIGS. 1-10) and a lump inductor (e.g., the inductor 1310 as shown in FIG. 13). It should be understood that method steps shown in FIG. 16A can be utilized and/or adapted to fabricate pressure sensors having other variable capacitors and other lump inductors (e.g., as shown in FIGS. 11, 12, 14 and 15). For ease of explanation, reference is made to a method for fabricating the pressure sensor having a variable capacitor and lump inductor shown in FIG. 13.

At stage 1605, a substrate 210, such as a silicon wafer, is provided. The substrate 210 may have a thickness of about 500 microns. The substrate 210 is etched, e.g., deep reactive-ion etching (DRIE). In the illustrated embodiment, DRIE may be used to etch partially through a central portion of the substrate 210 to form channels (for the eventual variable capacitor 200) and to form other channels 216 completely through the substrate 210 (for the eventual inductor 1310). The width of the channels 216 in the central portion of the substrate 210 may be about 20 microns, and the depth of the channels 216 in the central portion of the substrate 210 may be about 200 microns. The width of the other channels 216 formed through the substrate 210 may also be about 20 microns. A tissue anchor (not shown in FIG. 16A) may be created on the backside 214 of the substrate 210. One example of a suitable tissue anchor is described in U.S. Publication No. 2006/0247664, entitled "Micromachined Tissue Anchors for Securing Implants Without Sutures by E. Meng et al., the contents of which are incorporated herein by reference.

At stage 1610, a first insulative layer 520 (e.g., as shown in FIG. 5) is deposited over the top surface 212 of the substrate 210. The insulative layer 520 may be Parylene and may have a thickness of about 2 microns. As shown in FIG. 16A, the first Parylene layer 520 is applied and patterned to coat surfaces that were exposed as a result of the etching at stage 1605, i.e., the inner surfaces of the open channels 216 formed partially and completely through the substrate 210

At stage 1615, metal electroplating is performed on the open channels 216 that were formed through the substrate 210 so that these channels 216 are filled with metal 1311 (as further illustrated in FIG. 13). These metal-filled channels or lines 1311 will eventually form the high aspect ratio inductor 1310 that is integrated within the substrate 210.

At stage 1620, surface metallization is performed on channels 216 that were formed partially through the substrate 210, thereby forming a layer of metal 522 over the first Parylene layer 520 (as further illustrated in FIG. 5)

At stage 1625, a first sacrificial coating of photoresist 1626 is applied (e.g., by spin coating) over a portion of the substrate 210. The thickness of the first photoresist coating 1626 may be about 10 microns. One suitable photoresist 1626 that may be utilized with embodiments is a layer of AZ4620 type photoresist (supplied by Clariant Corp., Charlotte, N.C.). The photoresist 1626 may be hard-baked at about 120° C. for smoothing of edges and degassing purposes. In the illustrated embodiment, the first photoresist coating 1626 is applied over the metal-filled channels 1311 positioned between other open channels 216 formed partially through the substrate 210.

At stage 1630, Parylene is applied and patterned a second time to fill with Parylene open channels 216 that were previously coated with metal, and to coat the photoresist 1626 with Parylene. The second Parylene layer may have a thickness of about 2 microns and will eventually form capacitor elements 232 and the cross bar 234 (as further illustrated in FIGS. 2 and 13).

At stage 1635, a second sacrificial photoresist coating 1636 is applied and patterned over the second Parylene coating that forms capacitor elements 232 and cross bar 234 elements, over portions of the substrate 210 and over channels 216 filled with metal 1311. The thickness of the second photoresist coating 1636 may be about 15 microns.

At stage 1640, metal connections are formed on electrodes (not shown for clarity) for purposes of connecting the metal-filled channels 216 (inductor wires 1311) and capacitor elements or interdigitated electrodes.

At stage 1645, Parylene is applied and patterned a third time. The third Parylene coating may have a thickness of about 5 microns and forms the flexible member 220 and an intermediate member 236 that extends between the flexible member 220 and the cross bar 234 elements formed at stage 1635. In the illustrated embodiment, the third Parylene layer covers the second photoresist coating 1636, portions of the substrate 210 and metal filled channels 216. The third Parylene coating is applied over sections that will eventually form the variable capacitor 220 and other sections that will eventually form the lump inductor 1310.

At stage 1650, the backside 212 of the substrate 210 is etched, e.g., using DRIE, and at stage 1655, the first and second photoresist layers 1626, 1636 that were applied at stages 1625 and 1630 are stripped away, thereby releasing the device components.

More specifically, metal 1311 that fills the channels 216 formed through the entire substrate 210 form the high aspect ratio fixed inductor 1310 (as further illustrated in FIG. 13), the top electrode plates or capacitor elements 232 are joined by cross bar elements 234 and are connected to the intermediate member 236, which extends between the cross bar elements 234 and the flexible member 220 (as further illustrated in FIGS. 2-4 and 13), and the bottom electrode plates form projections or fingers 218 and corresponding channels 216 in which capacitor elements 232 move to vary capacitance.

Figure 16B:
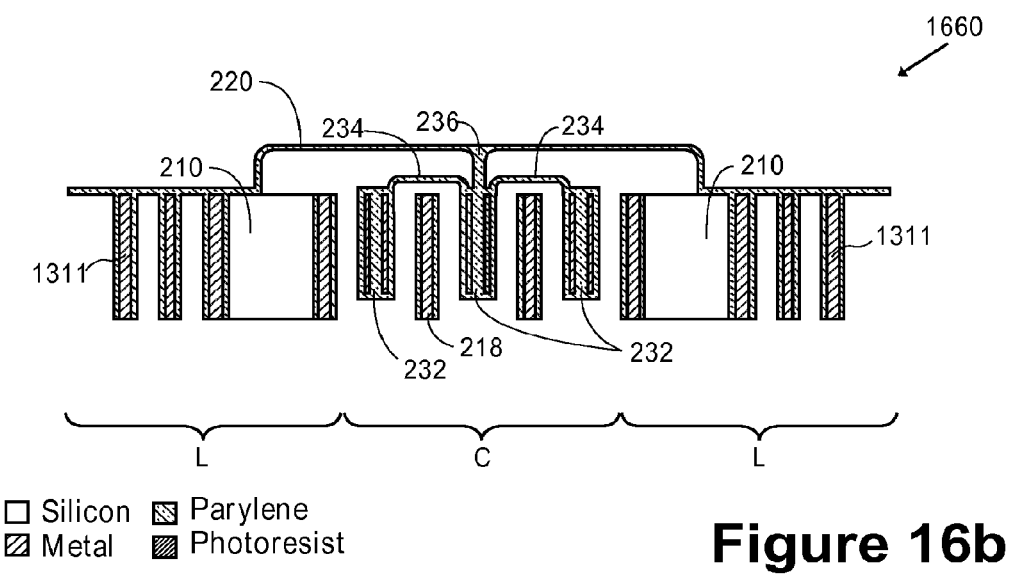
FIG. 16B illustrates an alternative sensor configuration having a variable capacitor and a variable inductor that can be fabricated using process steps shown in FIG. 16A.

It should be understood that method fabrication steps can be modified or adapted for fabrication of other structures of embodiments. The inductor may be a fixed inductor (e.g., as shown in FIG. 13), or method embodiments can be applied to fabricate a structure having a variable capacitor (as discussed above) and a variable inductor, e.g., as shown in FIG. 16B. The variable inductor shown in FIG. 16B may be formed by stage 1660 during which further etching 1660 of the silicon substrate 210 is performed to release the metal 1311 components and form a variable inductor. Thus, embodiments can be adapted for fabrication of various variable capacitor/lump inductor and variable capacitor/variable inductor configurations, and it should be understood that FIGS. 16A-B are provided to show examples of how embodiments may be implemented.

FIG. 17 is a table summarizing expected physical, electrical and microelectromechanical attributes of microfabricated pressure sensors having a variable capacitor as shown in FIGS. 1-10 and different lump inductors having fixed inductance as shown in FIGS. 12-15. Data in FIG. 17 was derived using finite element analysis and accepted electrical model calculations.

Embodiments advantageously provide microfabricated pressure sensors having sufficiently high capacitance, inductance, resonant frequency ($f_r$), fr shift ($\Delta f$) and sensitivity ($\Delta f/fr$), and sufficiently low resistance. For example, FIG. 17 shows that the pressure sensor 1200 shown in FIG. 12 has high inductance (about 40 nh), the pressure sensor 1300 shown in FIG. 13 low resistance (about 0.03 ohm) and a high Q factor (~600), and the pressure sensor 1400 shown in FIG. 14 has high inductance (about 145 nh) and high capacitance (about 127 pF). The pressure sensor 1300 including the high aspect ratio inductor 1310 has the lowest resistance (~0.03 ohm). Ratios of ($\Delta F/fr$) for all three pressure sensors 1200, 1300, 1400 were determined to exceed $10^{-3}$, indicating that sensor embodiments would be suitable for detection by an external measurement device of a telemetry system.

FIG. 17 also shows that microfabricated pressure sensors constructed according to embodiments should have sufficient sensitivity to be able to measure 1 mm Hg pressure changes, which correspond to a capacitance change of about 0.4 pF, while providing for a detection range of about 1-50 mmHg. FIG. 17 also shows that microfabricated pressure sensors that include a variable capacitor and inductors according to embodiments are advantageously sufficiently small in size so that they may be implanted through a clinical gauge needle and be implanted in various parts of an eye. For example, pressure sensors 1200 having the variable capacitor 200 (FIGS. 2-4) and the inductor 1210 (FIG. 12) or the inductor 1310 (FIG. 13) have dimensions of about 0.5 mm×0.5 mm 3.0 mm, and pressure sensors 1400 having the variable capacitor 200 (FIGS. 2-4) and the inductor 1410 including a rollable sheet has dimensions of about 0.5 mm×0.5 mm×4.0 mm (when in a stressed or compressed configuration). Other minimally invasive incisions may also be utilized if desired, e.g. incisions in the cornea that are smaller than about 3 mm to allow self-healing of the cornea. Further, tissue anchors may be utilized to implant sensor embodiments without the need for sutures, e.g., as described in U.S. Publication No. 2006/0247664, the contents of which were previously incorporated herein by reference.

Figure 18:
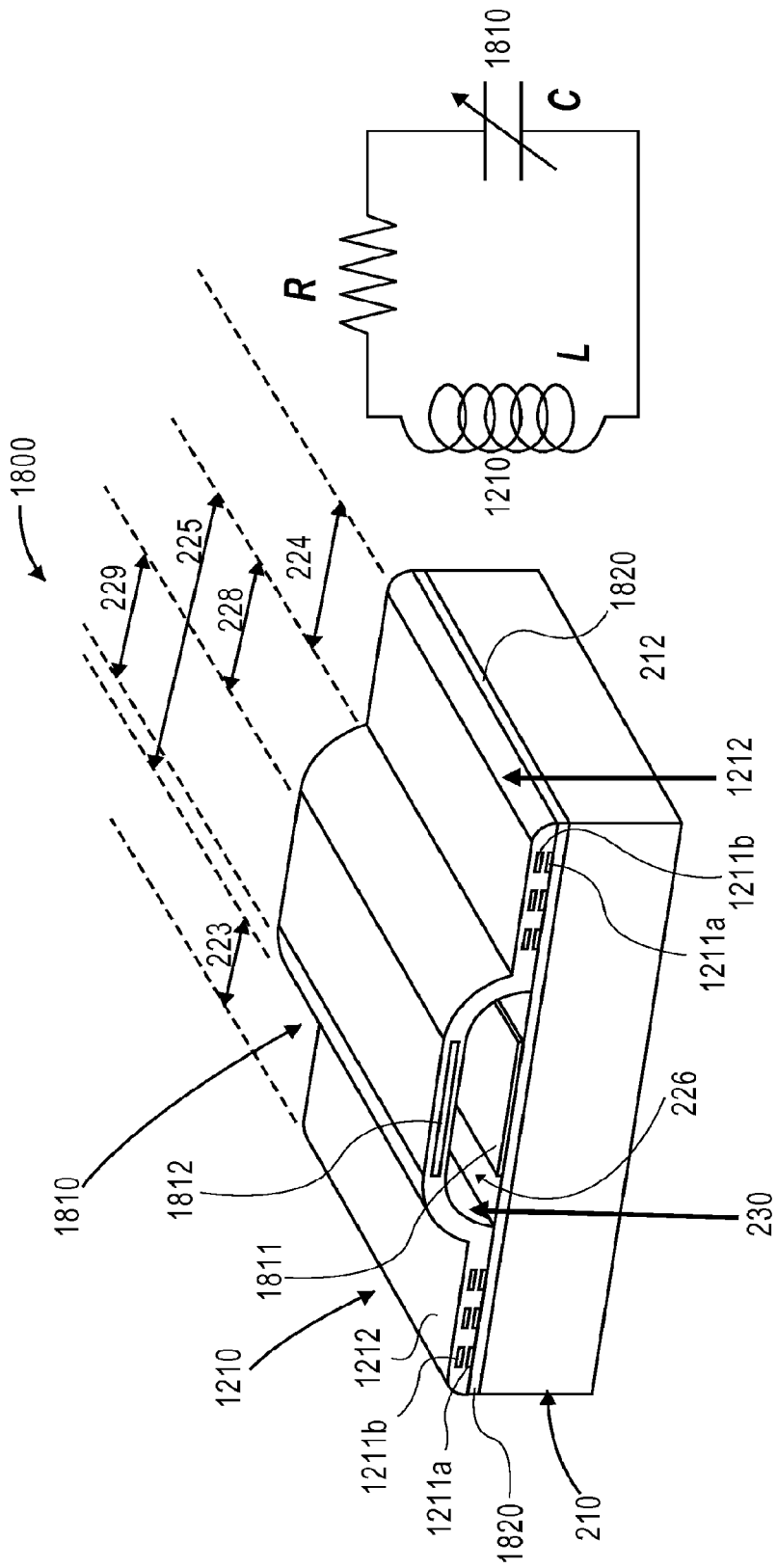
FIG. 18 is a perspective cross-sectional view of a microfabricated implantable pressure sensor including a variable capacitor, a lump inductor and a solid substrate according to another embodiment.

FIG. 18 illustrates another embodiment of an implantable microfabricated pressure sensor 1800 that includes a variable capacitor 1810 and a lump inductor, e.g., the inductor 1210 shown in FIG. 12. In the illustrated embodiment, the substrate 210 is a solid substrate (that does not include channels 216). As discussed above, the substrate 210 may, for example, be composed of silicon, a conductive polymer, or another suitable micromachinable substrate material having sufficiently high conductivity and may have a thickness of about 500 microns.

The variable capacitor 1810 is formed by one or more capacitor elements 1811 disposed on the top surface 212 of the substrate 210. The capacitor element 1811 is fixed and not movable. The variable capacitor 1810 also includes one or more capacitor elements 1812 that are carried by, e.g., embedded within, the flexible member 220. These capacitor elements 1812 are movable with the flexible member 220.

FIG. 18 illustrates an embodiment in which a single capacitor element 1811 or plate is positioned on the top surface 212 of the substrate 210 and extends along the length of the substrate 210, and a single capacitor element or plate 1812 is embedded within and extends along a length of the flexible member 220. In other embodiments, each capacitor element 1811, 1812 may be composed of multiple elements. Additionally, although the capacitor element 1812 is shown as being embedded within the flexible member 220, the capacitor element 1812 may also be carried by the flexible member 220, e.g. on a top surface 221 of the middle section 229 of the flexible member 220. FIG. 18 illustrates each capacitor element 1811, 1812 as a single component and the capacitor element 1812 being embedded within the flexible member 220 for ease of explanation and illustration.

Further, it should be understood that during fabrication of the sensor 1800, another material, such as a layer of silicon dioxide 1820 (shown in FIG. 18), may be applied on the top surface 212 of the substrate 210 for purposes of providing insulation between metal elements and the substrate 210. Thus, the capacitor element 1811 may be disposed on silicon dioxide 1820, but reference is made to the capacitor element 1811 being on the top surface 212, which includes being directly on the top surface 212 and a silicon dioxide layer 1820 that is applied on the top surface 212. The capacitor 1810 is eventually sealed so that the inner space or chamber 226 is also sealed and has a fixed internal or chamber pressure ($P_c$).

Figure 19:
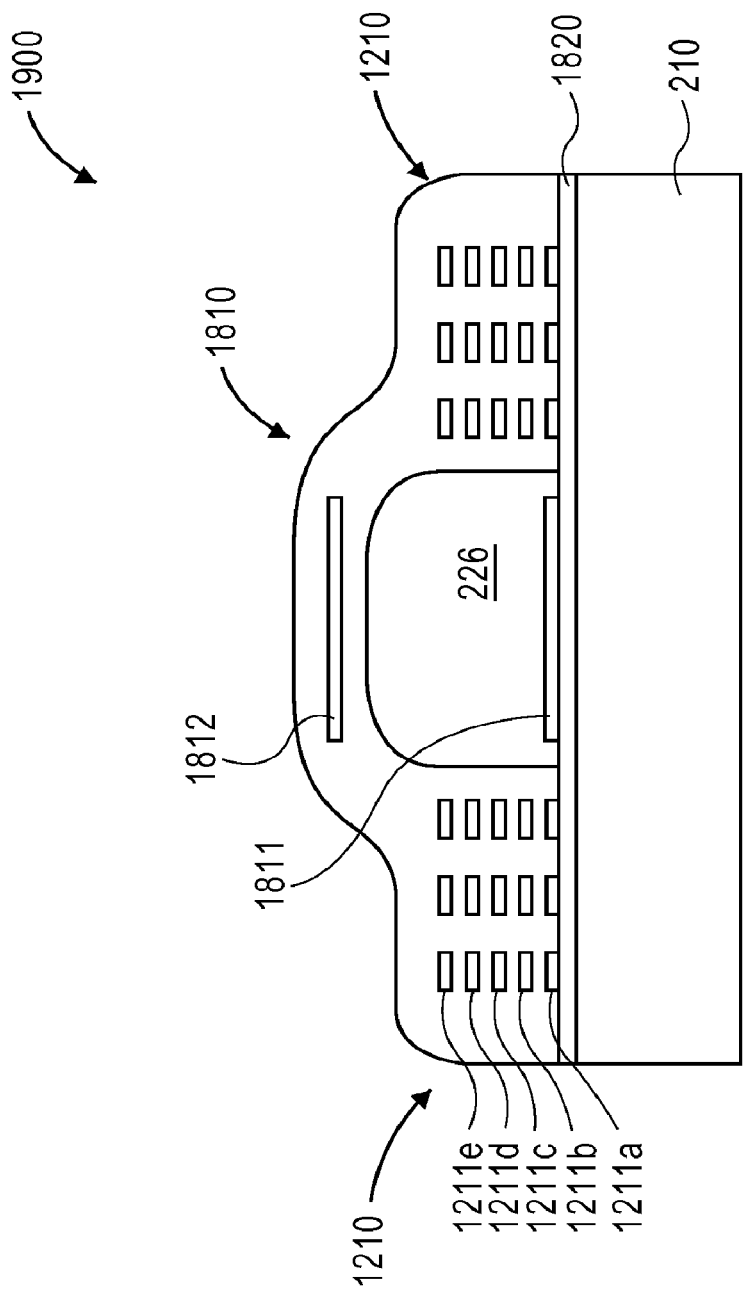
FIG. 19 is a cross-sectional view of another configuration of the pressure sensor shown in FIG. 18 having a lump inductor including multiple metallic layers.

The lump inductor 1210 may be configured as shown in FIG. 12 as a surface-micromachined stack of metallic layers 1211. FIG. 18 illustrates one embodiment in which the inductor 1210 includes a first or bottom layer 1211a and a second or top layer 1211b separated by an insulative material such as Parylene. The bottom metallic layer 1211a is disposed on the silicon dioxide 1820 layer and covered by the insulative material 1212, whereas the top metallic layer 1211b is embedded within insulative material 1212. Referring to FIG. 19, a pressure sensor 1900 may include additional layers of metallic elements, e.g., layers 1211a-e, in order to increase inductance as necessary.

In one embodiment, the bottom and top metallic layers 1211a, 1211b may have the same thickness, e.g., about 2 microns, the same width, e.g., about 20 microns, and the same length, e.g., about 3 millimeters. In another embodiment, the bottom metallic layer 1211a may be thicker than a top metallic layer 1211b in order to increase inductance while maintaining flexibility of the flexible member 220 in which the top metallic layer 1211b is embedded. For example, the bottom layer 1211a may have a thickness of about 2 microns, and the top layer 1211b may have a thickness of about 0.5 micron.

During use, if the pressure inside of the chamber 226 exceeds the external fluid pressure, the flexible member 220 will retain is original or initial shape. However, if the fluid pressure is greater than the internal chamber 226 pressure, then the flexible member 220 will deflect or be deformed by the fluid pressure, thereby moving at least the middle section 229 and the capacitor element 1812 embedded therein closer to the fixed capacitor element 1811 disposed on the top surface 212 of the substrate 210. Movement of the flexible member 220 alters the capacitance and the resonant frequency response of a sensor circuit 1800 since capacitance increases by decreasing the space between the capacitor elements 1811, 1812, and decreases by increasing the space between the capacitor elements 1811, 1812.

Figure 20:
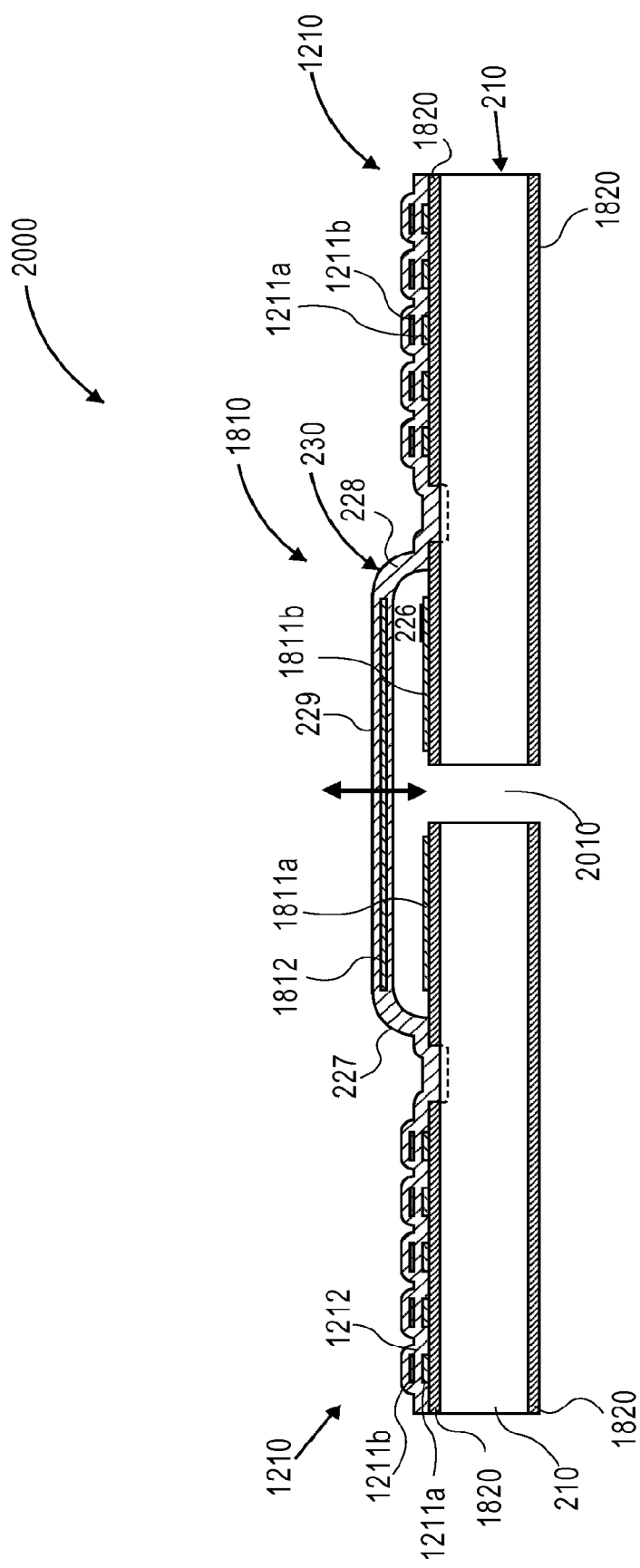
FIG. 20 is a cross-sectional view of a microfabricated implantable pressure sensor having a variable capacitor and a lump inductor constructed according to another embodiment.

FIG. 20 illustrates another embodiment of a microfabricated implantable pressure sensor 2000 that is configured as shown in FIG. 18 and includes a port 2010 that is formed through the substrate 210. The capacitor element 188 includes elements 1811a and 1811b within the chamber 226 and on each side of the port 2010. As discussed below with reference to FIG. 21, the port 2010 may be used to evacuate materials that are used during fabrication of the sensor 2010.

Figure 21:
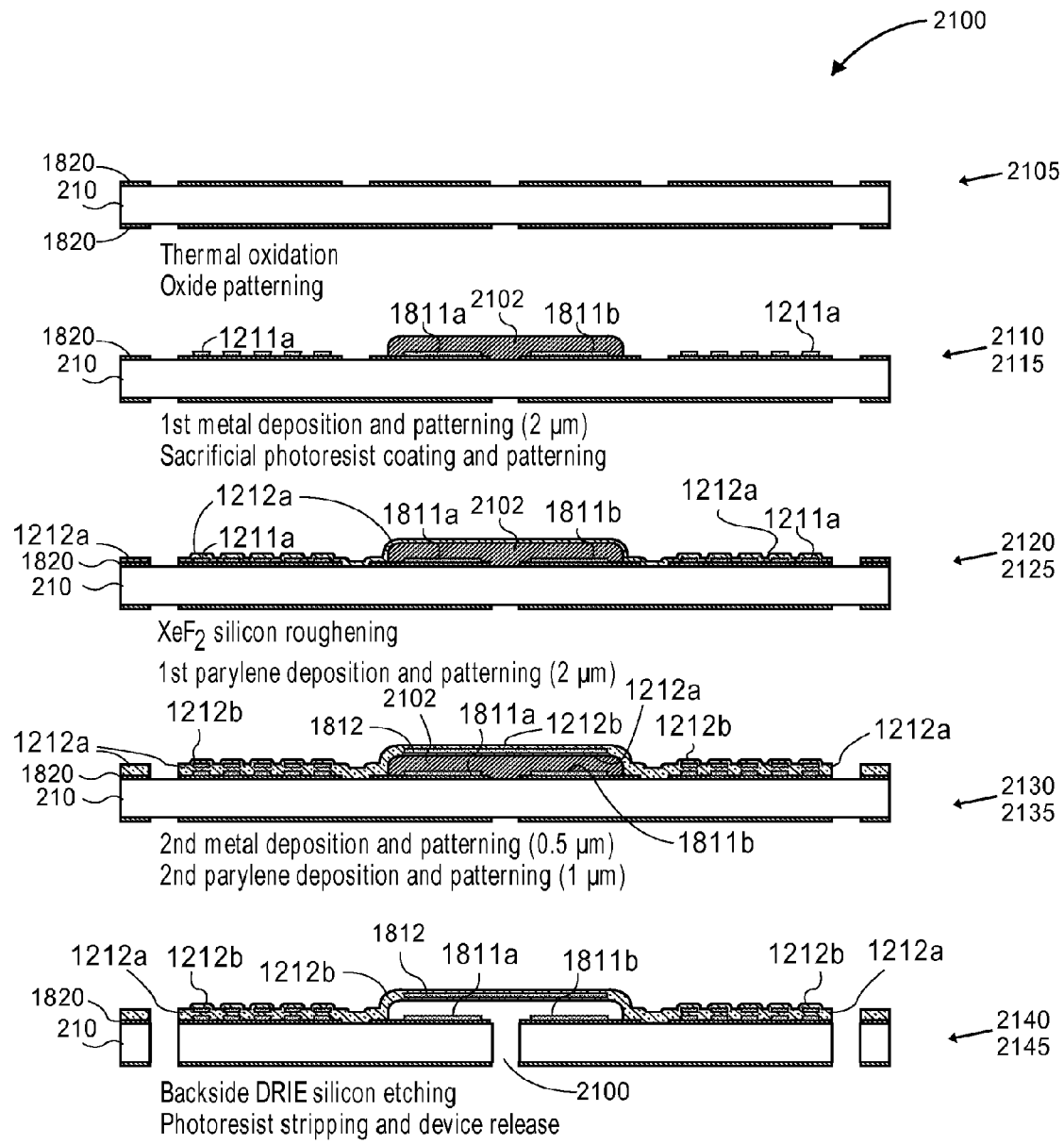
FIG. 21 is a flow diagram illustrating one embodiment of a method of fabricating an implantable pressure sensor constructed as shown in FIG. 20.

FIG. 21 is a flow chart of a method 2100 of fabricating an embodiment of micromachined pressure sensor 2000 having a variable capacitor, e.g., the variable capacitor 1810 shown in FIGS. 18-20, and a lump inductor, e.g., the inductor 1210 shown in FIGS. 12 and 18-20. It should be understood, however, that the method 2100 may be utilized and/or adapted to fabricate other sensors having other variable capacitor and lump inductor configurations. For ease of explanation, reference is made to a method 2100 for fabricating the pressure sensor 2000 having a variable capacitor 1810 and lump inductor 1210 shown in FIGS. 18 and 20.

At stage 2105, a substrate 210, such as a silicon wafer is provided. The substrate 210 may have a thickness of about 500 microns. The top and bottom surfaces 212, 214 of the substrate 210 may be processed by known thermal oxidation and oxide patterning methods. For example, a wet oxide (such as silicon dioxide layer 1820) having a thickness of about 1-2 microns may be grown on the top and bottom surfaces 212, 214 of the substrate 210.

At stage 2110, a first metal layer 1211a, 1811a, 1811b is deposited on the substrate 210, on the silicon dioxide layer 1820 on the top surface 212 of the substrate 210. The first metal layer 1211a may have a thickness of about 2 microns. Portions 1211a of the first metal layer will form part of the inductor 1210, and portions 1811a, 1811b of the metal layer will form the bottom or fixed component of the variable capacitor 1810.

At stage 2115, a sacrificial coating of photoresist 2102 is applied (e.g., by spin coating) over portions 1811a, 1811b of the first metal layer, over portions of silicon dioxide 1820, and over portions of the substrate 210. One suitable photoresist that may be utilized with embodiments is a layer of AZ4620 type photoresist (supplied by Clariant Corp., Charlotte, N.C.). The photoresist 2102 may be hard-baked at about 120° C. if applicable for smoothing of edges and degassing purposes.

At stage 2120, the top surface 212 of the silicon substrate 210 may be roughened using, e.g., $XeF_2$ gas-phase etching in order to promote adhesion of Parylene to the silicon substrate 210. At stage 2125, a first layer or coating of Parylene 1212a is deposited and patterned. As shown in FIG. 21, the first Parylene coating 1212a is applied over the photoresist 2102 and over metal layer portions 1212a that will eventually be a part of the lump inductor 1210 and is in contact with the silicon substrate 210 to form a seal. The first Parylene layer 1212a may have a thickness of about 2 microns.

At stage 2130, a second metal layer 1211b is deposited over the first Parylene layer 1212a. At stage 2135, a second Parylene layer 1212b is deposited and patterned. A portion of the second metal layer 1211b forms part of the inductor 1210, and another portion 1812 of the second metal layer forms the capacitor element carried by and movable with the flexible member 220.

At stage 2140, after the surface micromachining process and deposition of coatings or layers, silicon material is etched away from the backside 211 of the wafer 210 to create one or more through a holes, apertures or ports 2010. At stage 2145, photoresist 2102 is stripped away through the port 2010 using, e.g., acetone. Backside etching may be performed using, e.g., deep reactive-ion etching (DRIE). This, in turn, releases the flexible member 220.

Figure 22:
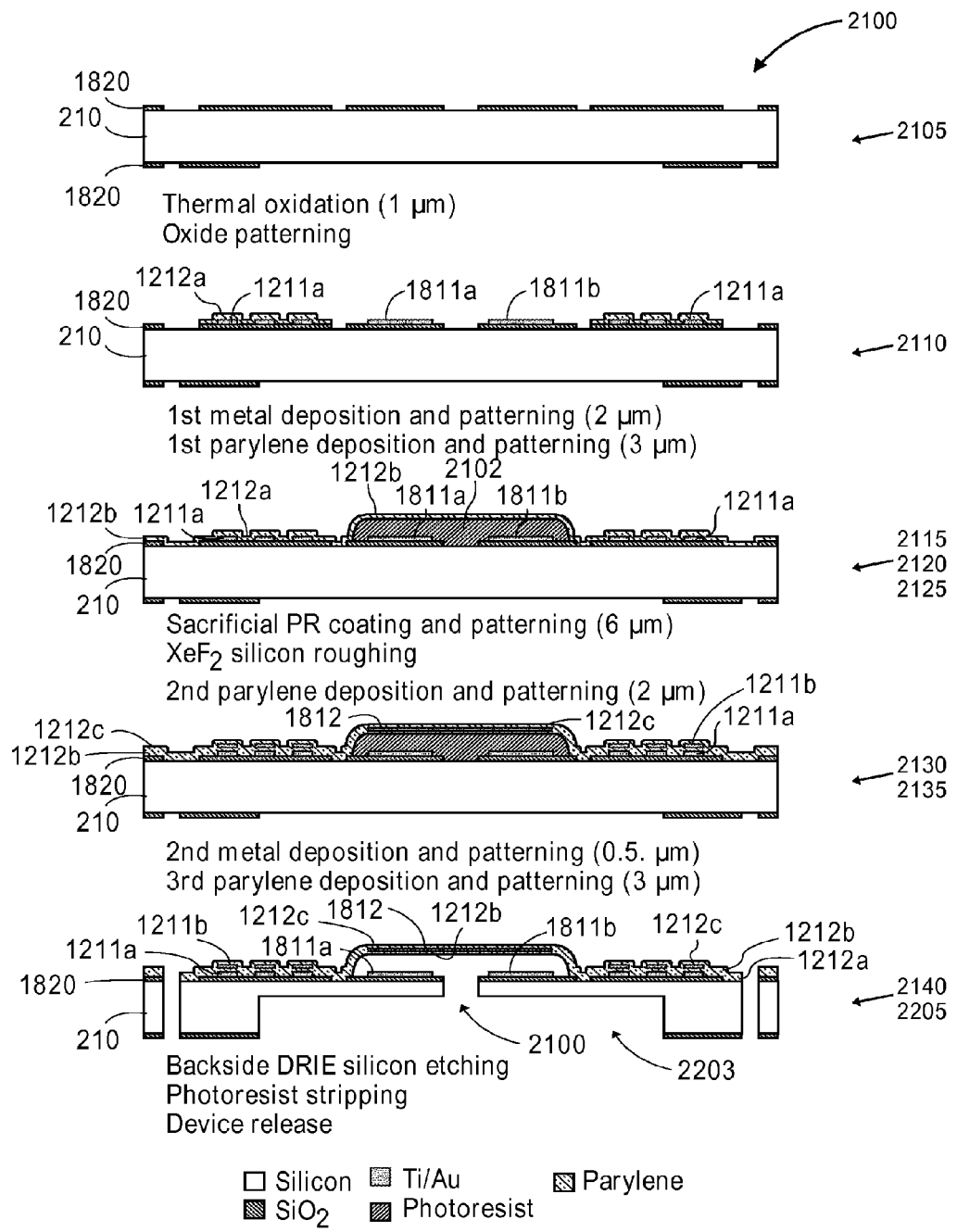
FIG. 22 is a flow diagram illustrating another embodiment of a method of fabricating an implantable pressure sensor having a recessed cavity on a backside of a substrate.

FIG. 22 illustrates a method 2200 that is similar to the method 2100 shown in FIG. 21, except that additional backside etching is performed at stage 2205 to form a recessed cavity 2203. The recessed cavity 2203 is advantageously increases the encapsulated air capacity after packaging of the pressure sensor.

FIG. 23 illustrates another embodiment of a pressure sensor 2300 that includes a variable capacitor 2310 a variable inductor 2320. In the illustrated embodiment, the substrate 210 is a solid substrate (that does not include channels 216). The variable capacitor 2310 is formed by one or more capacitor elements 1811 that are on the top surface 212 of the substrate 210. The illustrated embodiment includes one capacitor element 1811 that is fixed and not movable. One or more capacitor elements 1812 are carried by, e.g., embedded within, the flexible member 220, and movable with the flexible member 220.

FIG. 23 illustrates an embodiment in which a single capacitor element 1811 or plate is positioned on the top surface 212 of the substrate 210 and extends along the length of the substrate 210, and a single capacitor element or plate 1812 is embedded within and extends along a length of the flexible member 220. In other embodiments, capacitor elements 1811, 1812 may be composed of multiple elements. Additionally, although the capacitor element 1812 is shown as being embedded within the flexible member 220, the capacitor element 1812 may also be carried by the flexible member 220, e.g., on a top or outer surface 221 of the middle section 229 of the flexible member 220. FIG. 18 illustrates each capacitor element 1811, 1812 as a single component and the capacitor element 1812 being embedded within the flexible member 220 for ease of explanation. Further, as discussed above with respect to FIG. 18, the capacitor element 1811 is described as being on the top surface 212, although it may actually be on the silicon dioxide layer 1820.

The variable inductor 2320 includes a first or bottom layer 1211a and a second or top layer 1211b that is also embedded within the flexible member 220. For example, a first or bottom layer 1211a may be a metallic material having a thickness of about 2 microns, and the top layer 1211b may be a metallic material having a thickness of about 0.5 micron. The flexible member 220 may have a thickness of about 5 microns. Deformation or deflection of the flexible member 220 results in movement of portions of a variable capacitor 2310 and also movement of portions of the variable inductor 2320.

More specifically, if the internal chamber 226 pressure exceeds external fluid pressure, then the flexible member 220 will retain is original or initial shape. However, if the fluid pressure is greater than the internal chamber 226, then the flexible member 220 will deflect or be deformed by the fluid pressure, thereby moving at least the middle section 229 and simultaneously moving the capacitor element 1812 and inductor elements 1211b embedded therein. The capacitor element 1812 is moved closer to, and away from, the fixed capacitor element 1811 disposed on the top surface 212 of the substrate 210 with changes in fluid pressure, and inductor elements 1211b are also moved closer to, and away from, the fixed inductor elements 1211a, thereby simultaneously altering capacitance, inductance and resonant frequency response of the sensor 2300.

FIG. 24 illustrates another embodiment of a microfabricated implantable pressure sensor 2300 that is configured as shown in FIG. 23 and that includes a port 2010 formed through the substrate 210 and capacitor elements 1811a and 1811b within the chamber 226 and on each side of the port 2010. As discussed above with reference to FIGS. 20 and 21, the port 2010 may be used to evacuate photoresist materials that are used during fabrication of the sensor 2400. One manner in which the sensor 2400 shown in FIG. 20 may be fabricated is illustrated in FIG. 25.

Referring to FIG. 25, a method 2500 of fabricating a micromachined pressure sensor 2400 having a variable capacitor 2310 and a variable inductor 2320 includes providing a wafer or substrate 210, such as a silicon substrate, at stage 2505. The top and bottom surfaces of the substrate 210 are processed by known thermal oxidation and oxide patterning methods. For example, a wet oxide (such as silicon dioxide layer 1820) having a thickness of about 1-2 microns may be grown on the top and bottom surfaces of the silicon substrate 210 and patterned.

At stage 2510, a first metal layer 1211a, 1811a, 1811b is deposited on the silicon dioxide layer 1820 on the top surface 212 of the substrate 210. The first metal layer may have a thickness of about 2 microns. Portions 1211a of the first metal layer will form the bottom or fixed component of the inductor 1210, and portions 1811a, 1811b of the metal layer will form the bottom or fixed component of the variable capacitor 1810.

At stage 2515, a sacrificial coating of photoresist 2102 is applied (e.g., by spin coating) over portions 1211a, 1811a, 1811b of the first metal layer, portions of silicon dioxide 1820, and portions of the substrate 210. The photoresist 2102 may have a thickness of about 6 microns. Thus, in the illustrated embodiment, photoresist 2102 is applied over the entire metal layer, whereas in the embodiments shown in FIGS. 21 and 22, for example, photoresist 2102 is not applied over portions 1211a that will form part of the inductor 2110.

At stage 2520, the top surface 212 of the silicon substrate 210 may be roughened using, e.g., $XeF_2$ gas-phase etching, and at stage 2525, a first layer or coating of Parylene 1212a is deposited and patterned. As shown in FIG. 25, the first Parylene coating 1212a is applied over all of the photoresist 2102 and contacts the silicon substrate 210 to form a seal. The first Parylene layer 1212a may have a thickness of about 2 microns.

At stage 2530, a second metal layer 1211b, 1812 is deposited over the first Parylene layer 1212a. A portion of the second metal layer 1211b forms part of the variable inductor 2320, and another portion 1812 of the second metal layer forms part of the variable capacitor 2310, both of which are carried by and movable with the flexible member 220.

At stage 2535, a second Parylene layer 1212b is deposited over the second metal layer 1211b, 1812 and patterned. At stage 2540, after the surface micromachining process and deposition of coatings or layers, silicon material is etched away from the backside 211 of the wafer 210 to create one or more through a holes, apertures or ports 2000, and at stage 2545, photoresist 2102 is stripped away through the port 2000 using, e.g., acetone. Backside etching may be performed using, e.g., deep reactive-ion etching (DRIE). This, in turn, releases the flexible member, which may then move depending on external fluid pressure. FIG. 25 also illustrates an embodiment in which additional backside etching is performed a stage 2550 to form recessed cavity 2203, which may be usefully to increase the encapsulated air capacity after packaging of the pressure sensor. It should be understood that method 2100 steps can be utilized and/or adapted to fabricate variable capacitor 2310 and variable inductor 2320 configurations, and for ease of explanation, reference is made to a method for fabricating the pressure sensor having a variable capacitor 2310 and lump inductor 2320 as shown in FIGS. 23 and 24.

Although particular embodiments have been shown and described, it should be understood that the above discussion is not intended to limit the scope of these embodiments. Various changes and modifications may be made without departing from the spirit and scope of embodiments. For example, pressure sensors may include a variable capacitor and a lump inductor, or a variable capacitor and a variable inductor. Further, the dimensions and configurations of variable capacitor, lump inductor and variable inductor components are provided as examples of how embodiments may be implemented, and other dimensions and configurations may be utilized to suit pressure sensing specifications and applications. Further, fabrication process parameters and steps may vary with fabrication of different capacitor and inductor configurations. Although embodiments are described with reference to a polymer, e.g., Parylene, flexible member and capacitor elements may be other materials, e.g., a biocompatible metal, and may be the same or different materials. Embodiments may also be utilized with variable capacitors having capacitor elements that are movable within channels formed in a substrate and with variable capacitors that are implemented without substrate channels.

Although reference is made to ocular implantation of a sensor without sutures by delivering the sensor through a needle, it should be understood that other minimally invasive implantation procedures and devices may be utilized as needed. For example, sensor devices may be implanted through corneal or scleral incisions of a suitable size. Sensor devices may also be implanted using tissue anchors or hooks. It should also be understood that embodiments may be utilized in various biomedical applications. Although reference is made to a microfabricated pressure sensor for passive monitoring of intraocular pressure using telemetry, embodiments may also be used or adapted for use in other applications including, but not limited to, monitoring pressure of other bodily fluids and physiological parameters such as monitoring pressure of blood within an aneurysm, monitoring pressure of cerebrospinal fluid and monitoring pressure in other biomedical applications. Accordingly, embodiments are intended to cover alternatives, modifications, and equivalents that fall within the scope of the claims.

What is claimed is:

1. A variable capacitor of a microfabricated implantable pressure sensor, comprising:
   a substrate defining a plurality of channels;
   a flexible member having first and second edges on the substrate and a middle portion extending between the first and second edges and raised above the substrate to define a chamber between the substrate and the middle portion; and
   a plurality of capacitor elements extending indirectly from the flexible member, the plurality of capacitor elements being movable within respective channels with changes of fluid pressure on an outer surface of the flexible member, capacitance varying with changes in an overlapping area of the plurality of capacitor elements and the substrate.

2. The variable capacitor of claim 1, wherein the middle portion is deformable from a relaxed shape to a deformed shape when fluid pressure on the outer surface of the middle portion exceeds an interior chamber pressure, thereby increasing the overlapping area and capacitance.

3. The variable capacitor of claim 1, wherein the flexible member is made of a polymer or a parylene that has a Young's modulus of 1 GPa to 10 GPa.

4. The variable capacitor of claim 1, wherein the substrate is made of silicon or a conductive polymer.

5. The variable capacitor of claim 1, wherein the plurality of channels defines a first comb structure, the plurality of capacitor elements defining a second comb structure.

6. The variable capacitor of claim 1 further comprising a cross bar carrying the plurality of capacitor elements and an intermediate member extending between the flexible member and the cross bar.

7. The variable capacitor of claim 6, wherein the chamber is defined by the flexible member, the cross bar, and the intermediate member.

8. The variable capacitor of claim 1, wherein the substrate, the flexible member and the plurality of capacitor elements are configured for intraocular implantation through a needle.

9. The variable capacitor of claim 1 further comprising a silicon dioxide layer disposed between the substrate and the first and second edges of the flexible member.

* * * * *